US008626290B2

(12) United States Patent
Dagan et al.

(10) Patent No.: US 8,626,290 B2
(45) Date of Patent: Jan. 7, 2014

(54) ACUTE MYOCARDIAL INFARCTION TREATMENT BY ELECTRICAL STIMULATION OF THE THORACIC AORTA

(75) Inventors: Amir Dagan, Kibbutz Megiddo (IL); Yotam Reisner, Kiryat Tivon (IL); Offer Glasberg, Zichron Ya'akov (IL); Nitai Hanani, Haifa (IL); Gal Ariav, Givaat Ada (IL)

(73) Assignee: Enopace Biomedical Ltd., Caesarea Industrial Park (IL)

( * ) Notice: Subject to any disclaimer, the term of this patent is extended or adjusted under 35 U.S.C. 154(b) by 0 days.

(21) Appl. No.: 13/210,778

(22) Filed: Aug. 16, 2011

(65) Prior Publication Data
US 2012/0035679 A1 Feb. 9, 2012

Related U.S. Application Data

(63) Continuation-in-part of application No. 12/957,799, filed on Dec. 1, 2010, which is a continuation-in-part of application No. 12/792,227, filed on Jun. 2, 2010, which is a continuation-in-part of application No. PCT/IL2009/000117, filed on Jan. 29, 2009, which is a continuation-in-part of application No. 12/023,896, filed on Jan. 31, 2008, said application No. 12/957,799 is a continuation-in-part of application No. 12/851,214, filed on Aug. 5, 2010, now Pat. No. 8,538,535.

(60) Provisional application No. 61/183,319, filed on Jun. 2, 2009, provisional application No. 61/331,453, filed on May 5, 2010.

(51) Int. Cl.
*A61N 1/00* (2006.01)

(52) U.S. Cl.
USPC .......................................... 607/14

(58) Field of Classification Search
USPC ...................... 607/4, 5, 9, 14, 44
See application file for complete search history.

(56) References Cited

U.S. PATENT DOCUMENTS 3,650,277 A 3/1972 Sjostrand et al.
3,661,148 A 5/1972 Kolin
(Continued)

FOREIGN PATENT DOCUMENTS

EP 0109935 A1 5/1984
EP 0791341 A1 8/1997
(Continued)

OTHER PUBLICATIONS

An Office Action dated Oct. 2, 2012, which issued during the prosecution of U.S. Appl. No. 12/851,214.
(Continued)

*Primary Examiner* — Christopher D Koharski
*Assistant Examiner* — Nadia Ahmad
(74) *Attorney, Agent, or Firm* — Edwards Wildman Palmer LLP; Barry Kramer; Lisa Swiszcz

(57) ABSTRACT

Apparatus and methods are described including identifying a subject as suffering from a condition selected from the group consisting of congestive heart failure, diastolic heart failure, acute myocardial infarction, and hypertension. In response to the identifying, an electrode is placed on the subject's aorta at an aortic site that is between a bifurcation of the aorta with the subject's left subclavian artery and a bifurcation of the aorta with the subject's fifth intercostal artery. The subject is treated by electrically stimulating the aortic site by driving a current into the aortic site, via the electrode. Other applications are also described.

28 Claims, 14 Drawing Sheets

(56) References Cited

U.S. PATENT DOCUMENTS

| | | |
|---|---|---|
| 4,154,227 A | 5/1979 | Krause et al. |
| 4,201,219 A | 5/1980 | Bozal Gonzalez et al. |
| 4,474,630 A | 10/1984 | Planck et al. |
| 4,791,931 A | 12/1988 | Slate |
| 4,821,723 A | 4/1989 | Baker, Jr. et al. |
| 4,938,766 A | 7/1990 | Jarvik |
| 5,192,271 A | 3/1993 | Kalb et al. |
| 5,265,011 A | 11/1993 | O'Rourke |
| 5,265,601 A | 11/1993 | Mehra |
| 5,324,323 A | 6/1994 | Bui |
| 5,330,507 A | 7/1994 | Schwartz |
| 5,372,573 A | 12/1994 | Habib |
| 5,411,031 A | 5/1995 | Yomtov |
| 5,423,871 A | 6/1995 | Hoegnelid et al. |
| 5,458,626 A | 10/1995 | Krause |
| 5,487,760 A | 1/1996 | Villafana |
| 5,612,314 A | 3/1997 | Stamler et al. |
| 5,645,839 A | 7/1997 | Chobanian et al. |
| 5,649,966 A | 7/1997 | Noren et al. |
| 5,669,924 A | 9/1997 | Shaknovich |
| 5,707,400 A | 1/1998 | Terry, Jr. et al. |
| 5,762,599 A | 6/1998 | Sohn |
| 5,782,774 A | 7/1998 | Shmulewitz |
| 5,800,464 A | 9/1998 | Kieval |
| 5,800,502 A | 9/1998 | Boutos |
| 5,900,433 A | 5/1999 | Igo et al. |
| 5,902,712 A | 5/1999 | Burns et al. |
| 5,904,712 A | 5/1999 | Axelgaard |
| 5,906,641 A | 5/1999 | Thompson et al. |
| 5,913,876 A | 6/1999 | Taylor et al. |
| 5,935,077 A | 8/1999 | Ogle |
| 5,994,444 A | 11/1999 | Trescony et al. |
| 6,023,640 A | 2/2000 | Ross |
| 6,038,485 A | 3/2000 | Axelgaard |
| 6,053,873 A | 4/2000 | Govari et al. |
| 6,058,331 A | 5/2000 | King |
| 6,086,527 A | 7/2000 | Talpade |
| 6,106,477 A | 8/2000 | Miesel et al. |
| 6,120,520 A | 9/2000 | Saadat et al. |
| 6,141,587 A | 10/2000 | Mower |
| 6,200,259 B1 | 3/2001 | March |
| 6,245,103 B1 | 6/2001 | Stinson |
| 6,277,078 B1 | 8/2001 | Porat et al. |
| 6,280,377 B1 | 8/2001 | Talpade |
| 6,347,247 B1 | 2/2002 | Dev et al. |
| 6,411,845 B1 | 6/2002 | Mower |
| 6,445,953 B1 | 9/2002 | Bulkes et al. |
| 6,463,323 B1 | 10/2002 | Conrad-Vlasak et al. |
| 6,485,524 B2 | 11/2002 | Strecker |
| 6,522,926 B1 | 2/2003 | Kieval et al. |
| 6,575,994 B1 | 6/2003 | Marin et al. |
| 6,616,613 B1 | 9/2003 | Goodman |
| 6,616,624 B1 | 9/2003 | Kieval |
| 6,622,041 B2 | 9/2003 | Terry, Jr. et al. |
| 6,632,991 B2 | 10/2003 | Chen |
| 6,647,287 B1 | 11/2003 | Peel, III et al. |
| 6,721,603 B2 | 4/2004 | Zabara et al. |
| 6,810,286 B2 | 10/2004 | Donovan et al. |
| 6,824,561 B2 | 11/2004 | Soykan et al. |
| 6,845,267 B2 | 1/2005 | Harrison et al. |
| 6,850,801 B2 | 2/2005 | Kieval et al. |
| 6,865,416 B2 | 3/2005 | Dev et al. |
| 6,871,092 B2 | 3/2005 | Piccone |
| 6,885,895 B1 | 4/2005 | Whitehurst et al. |
| 6,939,345 B2 | 9/2005 | KenKnight et al. |
| 6,947,792 B2 | 9/2005 | Ben-Haim et al. |
| 6,985,774 B2 | 1/2006 | Kieval et al. |
| 7,044,981 B2 | 5/2006 | Liu et al. |
| 7,062,318 B2 | 6/2006 | Ben-Haim et al. |
| 7,082,336 B2 | 7/2006 | Ransbury et al. |
| 7,090,648 B2 | 8/2006 | Sackner et al. |
| 7,158,832 B2 | 1/2007 | Kieval et al. |
| 7,167,751 B1 | 1/2007 | Whitehurst et al. |
| 7,206,637 B2 | 4/2007 | Salo |
| 7,225,019 B2 | 5/2007 | Jahns et al. |
| 7,229,403 B2 | 6/2007 | Schock et al. |
| 7,269,457 B2 | 9/2007 | Shafer et al. |
| 7,291,113 B2 | 11/2007 | Satoh et al. |
| 7,292,886 B1 | 11/2007 | Kroll |
| 7,299,091 B2 | 11/2007 | Barrett et al. |
| 7,389,149 B2 | 6/2008 | Rossing et al. |
| 7,395,119 B2 | 7/2008 | Hagen et al. |
| 7,452,334 B2 | 11/2008 | Gianchandani et al. |
| 7,476,200 B2 | 1/2009 | Tal |
| 7,486,991 B2 | 2/2009 | Libbus et al. |
| 7,614,998 B2 | 11/2009 | Gross et al. |
| 7,623,926 B2 | 11/2009 | Rossing et al. |
| 7,706,884 B2 | 4/2010 | Libbus |
| 7,706,886 B2 | 4/2010 | Morimoto et al. |
| 7,747,302 B2 | 6/2010 | Milledge et al. |
| 7,765,000 B2 | 7/2010 | Zhang et al. |
| 7,811,221 B2 | 10/2010 | Gross |
| 2001/0044434 A1 | 11/2001 | Lee et al. |
| 2002/0016615 A1 | 2/2002 | Dev et al. |
| 2002/0026228 A1 | 2/2002 | Schauerte |
| 2002/0032468 A1 | 3/2002 | Hill et al. |
| 2002/0077554 A1 | 6/2002 | Schwartz et al. |
| 2002/0103454 A1 | 8/2002 | Sackner et al. |
| 2002/0169413 A1 | 11/2002 | Keren et al. |
| 2003/0036773 A1 | 2/2003 | Whitehurst et al. |
| 2003/0050683 A1 | 3/2003 | Boutos |
| 2003/0060858 A1 | 3/2003 | Kieval et al. |
| 2003/0130715 A1 | 7/2003 | Boutos |
| 2003/0199806 A1 | 10/2003 | Kieval |
| 2003/0204206 A1 | 10/2003 | Padua et al. |
| 2004/0010303 A1 | 1/2004 | Bolea et al. |
| 2004/0019364 A1 | 1/2004 | Kieval et al. |
| 2004/0039417 A1 | 2/2004 | Soykan et al. |
| 2004/0044393 A1 | 3/2004 | Yarden et al. |
| 2004/0054384 A1 | 3/2004 | Nachum |
| 2004/0064090 A1 | 4/2004 | Keren et al. |
| 2004/0106954 A1* | 6/2004 | Whitehurst et al. ............... 607/3 |
| 2004/0106976 A1 | 6/2004 | Bailey et al. |
| 2004/0111006 A1 | 6/2004 | Alferness et al. |
| 2004/0133240 A1 | 7/2004 | Adams et al. |
| 2004/0162590 A1 | 8/2004 | Whitehurst et al. |
| 2004/0193092 A1 | 9/2004 | Deal |
| 2004/0254616 A1 | 12/2004 | Rossing et al. |
| 2005/0027346 A1 | 2/2005 | Arkusz et al. |
| 2005/0033407 A1 | 2/2005 | Weber et al. |
| 2005/0090867 A1 | 4/2005 | Lapanashvili et al. |
| 2005/0096710 A1 | 5/2005 | Kieval |
| 2005/0143785 A1 | 6/2005 | Libbus |
| 2005/0149130 A1 | 7/2005 | Libbus |
| 2005/0149132 A1 | 7/2005 | Libbus |
| 2005/0149155 A1 | 7/2005 | Scheiner et al. |
| 2005/0154418 A1 | 7/2005 | Kieval et al. |
| 2005/0203610 A1 | 9/2005 | Tzeng |
| 2005/0209652 A1 | 9/2005 | Whitehurst et al. |
| 2005/0232965 A1 | 10/2005 | Falotico |
| 2005/0233962 A1 | 10/2005 | Lue et al. |
| 2005/0240229 A1 | 10/2005 | Whitehurst et al. |
| 2005/0251212 A1 | 11/2005 | Kieval et al. |
| 2006/0004417 A1 | 1/2006 | Rossing et al. |
| 2006/0004420 A1 | 1/2006 | Rossing et al. |
| 2006/0004430 A1 | 1/2006 | Rossing et al. |
| 2006/0074453 A1 | 4/2006 | Kieval et al. |
| 2006/0100668 A1 | 5/2006 | Ben-David et al. |
| 2006/0111626 A1 | 5/2006 | Rossing et al. |
| 2006/0149124 A1 | 7/2006 | Forsell |
| 2006/0149345 A1 | 7/2006 | Boggs et al. |
| 2006/0167540 A1 | 7/2006 | Masters et al. |
| 2006/0173507 A1 | 8/2006 | Mrva et al. |
| 2006/0217588 A1 | 9/2006 | Gross et al. |
| 2006/0217772 A1 | 9/2006 | Libbus et al. |
| 2006/0229677 A1 | 10/2006 | Moffitt et al. |
| 2006/0259085 A1 | 11/2006 | Zhang et al. |
| 2006/0265038 A1 | 11/2006 | Hagen et al. |
| 2006/0276844 A1 | 12/2006 | Alon et al. |
| 2006/0293712 A1 | 12/2006 | Kieval et al. |
| 2007/0021673 A1 | 1/2007 | Arbel et al. |
| 2007/0021786 A1 | 1/2007 | Parnis et al. |
| 2007/0021790 A1 | 1/2007 | Kieval et al. |
| 2007/0021792 A1* | 1/2007 | Kieval et al. ............... 607/23 |

(56) References Cited

U.S. PATENT DOCUMENTS

| | | |
|---|---|---|
| 2007/0021794 A1 | 1/2007 | Kieval et al. |
| 2007/0021796 A1 | 1/2007 | Kieval et al. |
| 2007/0021797 A1 | 1/2007 | Kieval et al. |
| 2007/0021798 A1 | 1/2007 | Kieval et al. |
| 2007/0021799 A1 | 1/2007 | Kieval et al. |
| 2007/0027496 A1 | 2/2007 | Parnis et al. |
| 2007/0038255 A1 | 2/2007 | Kieval et al. |
| 2007/0038259 A1 | 2/2007 | Kieval et al. |
| 2007/0038260 A1 | 2/2007 | Kieval et al. |
| 2007/0038261 A1 | 2/2007 | Kieval et al. |
| 2007/0038262 A1 | 2/2007 | Kieval et al. |
| 2007/0049989 A1 | 3/2007 | Rossing et al. |
| 2007/0060972 A1 | 3/2007 | Kieval et al. |
| 2007/0106340 A1 | 5/2007 | Bolea et al. |
| 2007/0142879 A1 | 6/2007 | Greenberg et al. |
| 2007/0150009 A1 | 6/2007 | Kveen et al. |
| 2007/0156179 A1 | 7/2007 | S.E. |
| 2007/0156198 A1 | 7/2007 | Rossing et al. |
| 2007/0156201 A1 | 7/2007 | Rossing |
| 2007/0167984 A1 | 7/2007 | Kieval et al. |
| 2007/0185542 A1 | 8/2007 | Bolea et al. |
| 2007/0185543 A1 | 8/2007 | Rossing et al. |
| 2007/0196428 A1 | 8/2007 | Glauser et al. |
| 2007/0198064 A1 | 8/2007 | Lapanashvili et al. |
| 2007/0815543 | 8/2007 | Rossing et al. |
| 2007/0248676 A1 | 10/2007 | Stamler et al. |
| 2007/0248850 A1 | 10/2007 | Heller |
| 2007/0276270 A1 | 11/2007 | Tran |
| 2007/0276442 A1 | 11/2007 | Hagen et al. |
| 2007/0276459 A1 | 11/2007 | Rossing et al. |
| 2007/0282385 A1 | 12/2007 | Rossing et al. |
| 2007/0293927 A1 | 12/2007 | Frank et al. |
| 2008/0004673 A1 | 1/2008 | Rossing et al. |
| 2008/0009916 A1 | 1/2008 | Rossing et al. |
| 2008/0009917 A1 | 1/2008 | Rossing et al. |
| 2008/0021336 A1 | 1/2008 | Dobak |
| 2008/0033501 A1 | 2/2008 | Gross |
| 2008/0046016 A1 | 2/2008 | Ben-David et al. |
| 2008/0046054 A1 | 2/2008 | Hjelle et al. |
| 2008/0051767 A1 | 2/2008 | Rossing et al. |
| 2008/0058872 A1 | 3/2008 | Brockway et al. |
| 2008/0071363 A1 | 3/2008 | Tuval et al. |
| 2008/0082137 A1 | 4/2008 | Kieval et al. |
| 2008/0097540 A1 | 4/2008 | Bolea et al. |
| 2008/0119898 A1 | 5/2008 | Ben-David et al. |
| 2008/0119911 A1 | 5/2008 | Rosero |
| 2008/0132972 A1 | 6/2008 | Shuros et al. |
| 2008/0140167 A1 | 6/2008 | Hagen et al. |
| 2008/0154349 A1 | 6/2008 | Rossing et al. |
| 2008/0161865 A1 | 7/2008 | Hagen |
| 2008/0161887 A1 | 7/2008 | Hagen |
| 2008/0167690 A1 | 7/2008 | Cody et al. |
| 2008/0167693 A1 | 7/2008 | Kieval et al. |
| 2008/0167694 A1 | 7/2008 | Bolea et al. |
| 2008/0167696 A1 | 7/2008 | Cates et al. |
| 2008/0167699 A1 | 7/2008 | Kieval et al. |
| 2008/0171923 A1 | 7/2008 | Bolea et al. |
| 2008/0172101 A1 | 7/2008 | Bolea et al. |
| 2008/0172104 A1 | 7/2008 | Kieval et al. |
| 2008/0177364 A1 | 7/2008 | Bolea et al. |
| 2008/0195174 A1 | 8/2008 | Walker et al. |
| 2008/0215117 A1 | 9/2008 | Gross |
| 2009/0036975 A1 | 2/2009 | Ward et al. |
| 2009/0062874 A1 | 3/2009 | Tracey et al. |
| 2009/0198097 A1 | 8/2009 | Gross |
| 2009/0198308 A1 | 8/2009 | Gross et al. |
| 2009/0204170 A1 | 8/2009 | Hastings et al. |
| 2009/0228078 A1 | 9/2009 | Zhang et al. |
| 2010/0010556 A1 | 1/2010 | Zhao et al. |
| 2010/0076247 A1 | 3/2010 | Zilbershlag et al. |
| 2010/0094373 A1 | 4/2010 | Sharma |
| 2010/0211131 A1 | 8/2010 | Williams et al. |
| 2010/0305392 A1 | 12/2010 | Gross et al. |
| 2011/0137370 A1 | 6/2011 | Gross et al. |

FOREIGN PATENT DOCUMENTS

| | | |
|---|---|---|
| WO | WO-9926530 A1 | 6/1999 |
| WO | WO-0002501 A1 | 1/2000 |
| WO | WO-0226314 A1 | 4/2002 |
| WO | WO-03076008 A1 | 9/2003 |
| WO | WO-03082080 A2 | 10/2003 |
| WO | WO-03082403 A2 | 10/2003 |
| WO | WO-2004014456 A2 | 2/2004 |
| WO | WO-2004073484 A2 | 9/2004 |
| WO | WO-2005065771 A1 | 7/2005 |
| WO | WO-2005084389 A2 | 9/2005 |
| WO | WO-2005097256 A2 | 10/2005 |
| WO | WO-2006012033 A2 | 2/2006 |
| WO | WO-2006012050 A2 | 2/2006 |
| WO | WO-2006032902 A1 | 3/2006 |
| WO | WO-2006041664 A2 | 4/2006 |
| WO | WO-2006064503 A2 | 6/2006 |
| WO | WO-2006/098928 A1 | 9/2006 |
| WO | WO-2006094273 A2 | 9/2006 |
| WO | WO-2006123346 A2 | 11/2006 |
| WO | WO-2006125163 A2 | 11/2006 |
| WO | WO-2007013065 A2 | 2/2007 |
| WO | WO-2007047152 A2 | 4/2007 |
| WO | WO-2007064895 A2 | 6/2007 |
| WO | WO-2007106533 A1 | 9/2007 |
| WO | WO-2007113818 A2 | 10/2007 |
| WO | WO-2007113833 A2 | 10/2007 |
| WO | WO-2007114860 A2 | 10/2007 |
| WO | WO-2007118090 A2 | 10/2007 |
| WO | WO-2007136850 A2 | 11/2007 |
| WO | WO-2007136851 A2 | 11/2007 |
| WO | WO-2008039982 A2 | 4/2008 |
| WO | WO-2008083120 A2 | 7/2008 |
| WO | WO-2008083235 A2 | 7/2008 |
| WO | WO-2008100390 A1 | 8/2008 |
| WO | WO-2009/017647 A1 | 2/2009 |
| WO | WO-2009095918 A2 | 8/2009 |
| WO | WO-2009095920 A2 | 8/2009 |

OTHER PUBLICATIONS

An Office Action dated Sep. 18, 2012, which issued during the prosecution of U.S. Appl. No. 12/023,896.

An English Translation of an Office Action dated Oct. 8, 2012, which issued during the prosecution of Chinese Patent Application No. 200980111617.8.

An Office Action dated Jun. 19, 2012, which issued during the prosecution of U.S. Appl. No. 11/995,904.

An Office Action dated Aug. 29, 2012, which issued during the prosecution of U.S. Appl. No. 12/792,227.

An Office Action dated Aug. 1, 2012, which issued during the prosecution of U.S. Appl. No. 12/957,799.

An International Search Report and a Written Opinion both dated Jul. 5, 2012, which issued during the prosecution of Applicant's PCT/IL11/00952.

Baudrie, Am J, "Optimal frequency ranges for extracting information on cardiovascular autonomic control from the blood pressure and pulse interval spectrograms in mice," Physiol Regul Integr Comp Physiol 292: R904-R912, 2007.

Biosense Webster, Inc. (CA, USA) manufactures the LASSO 2515 Variable Circular Mapping Catheter, 2010.

Cheetah Medical Inc.—FDA Approves Cheetah Reliant for Noninvasive Cardiac Output Monitoring, website article, Jan. 23, 2008.

Zhao G. et al., "Loss of nitric oxide production in the coronary circulation after the development of dilated cardiomyopathy: a specific defect in the neural regulation of coronary blood flow," Clinical and Experimental Pharmacology and Physiology 23(8): 715-721 (1996).

Hamilton et al., "Coronary vascular sympathetic beta-receptor innervation," American Journal of Physiology, vol. 230, No. 6, Jun. 1976.

Hayashida, et al., "Comparison of neurogenic contraction and relaxation in canine corpus cavernosum and penile artery and vein", Jpn. J. Pharmacol. 72:231-240 (1996), p. 232 col. 2, para 1; p. 238, col. 2, para 2.

(56) References Cited

OTHER PUBLICATIONS

Shin, J. H et al.,"Improving the biocompatibility of in vivo sensors via nitric oxide release," The Analyst, 2006, 131, pp. 609-615.
Kass, D., "Clinical evaluation of left heart function by conductance catheter technique," Eur Heart J. Nov. 13, 1992, Suppl E. pp. 57-64.
Katare R. G. et al. "Vagal nerve stimulation prevents reperfusion injury through inhibition of opening of mitochondrial permeability transition pore independent of the bradycardiac effect". J Thorac Cardiovasc Surg. Jan. 2009;137(1):223-31.
Kawada T. et al. "Vagal stimulation suppresses ischemia-induced myocardial interstitial myoglobin release". Life Sci. Sep. 26, 2008;83(13-14):490-5.
Kong S. et al., "Tumour necrosis factor-α and its receptors in the beneficial effects of vagal stimulation after myocardial infarction in rats," Clin Exp Pharmacol Physiol. 2011; 38:300-306.
Kugiyama K., et al., "Nitric oxide activity is deficient in spasm arteries of patients with coronary spastic angina," Circulation 94: 266-272 (1996).
Laitinen et al., "Sympathovagal balance is major determinant of short-term blood pressure variability in healthy subjects," Physiol Heart Circ Physiol 276:1245-1252, 1999.
Lewis et al., "Vagus nerve stimulation decreases left ventricular contractility in vivo in the human and pig heart," J Physiol. Jul. 15, 2001; 534(Pt 2): 547-552.
Malpas, "Neural influences on cardiovascular variability: possibilities and pitfalls," Am J Physiol Heart Circ Physiol 282: H6-H20, 2002.
Matheny, "Vagus nerve stimulation as a method to temporarily slow or arrest the heart," Ann Thorac Surg. Jun. 1997;63(6 Suppl):S28-9. Abstract only.
Frost, M.C. et al. "Preparation and characterization of implantable sensors with nitric oxide release coatings," Microchemical Journal vol. 74 Issue: 3, Jun. 2003 pp. 277-288.
Schoenfisch, M.H., et al., "Improving the thromboresistivity of chemical sensors via nitric oxide release: fabrication and in vivo evaluation of NO-releasing oxygen-sensing catheters," Anal. Chem., 72 (6), pp. 1119-1126, 2000.
Mioni et al. "Activation of an efferent cholinergic pathway produces strong protection against myocardial ischemia/reperfusion injury in rats". Crit Care Med. Nov. 2005;33(11):2621-8.
Paulus, W.J., "Beneficial effects of nitric oxide on cardiac diastolic function: the flip side of the coin," Heart Failure Review 5(4):pp. 337-344 (2000)—Abstract only.
Sabbah H et al., "Global left ventricular remodeling with the Acorn Cardiac Support Device: Hemodynamic and angiographic findings in dogs with heart failure," Heart Failure Reviews 10(2):109-115 (2005) first page.
Yao S-K, et al., "Endogenous and exogenous nitric oxide protect against intracoronary thrombosis and reocclusion after thrombolysis," Circulation. 1995; 92: pp. 1005-1010.
Sherman, AJ. et al., "Blockade of nitric oxide synthesis reduces myocardial oxygen consumption in vivo," Circulation 95:pp. 1328-1334 (1997).
Steendijk, P. et al. "Pressure-volume measurements by cnoductance catheter during cardiac resynchronization therapy," European Heart Journal (2004) 6 (Supplement D), D35-D42.
Suga, H. et al., "Ventricular systolic pressure-volume area as predictor of cardiac oxygen consumption," Am J Physiol. Jan. 1981: 240(1): H39-44.
Sulzer IntraTherapeutics Inc., "Intracoil® Self-Exanding Periphearl Stent," Brief description of FDA approval, Jun. 28, 2002.

Task Force of the European Society of Cardiology and the North American Society of Pacing and Electrophysiology "Heart rate variability," European Heart Journal (1996) 17, pp. 354-381.
Taylor, "The unequal influences of the left and right vagi on the control of the heart and pulmonary artery in the rattlesnake, *Crotalus durissus*," The Journal of Experimental Biology 212, pp. 145-151, 2009.
Uemura, K. et al., "Efferent vagal nerve stimulation induces tissue inhibitor of metalloproteinase-1 in myocardial ischemia-reperfusion injury in rabbit". Am J Physiol Heart Circ Physiol. Oct. 2007; 293(4):H2254-61.
Uemura et al., "Early short-term vagal nerve stimulation attenuates cardiac remodeling after reperfused myocardial infarction," J Card Fail. Aug. 2010; 16(8): 689-699; Abstract only.
Vallais. F. et al., "Heart rate and vasomotor control during exercise," Proceedings of the 29th Annual International Conference of the IEEE EMBS, Cité Internationale, Lyon, France, Aug. 23-26, 2007; 578-581.
Web page relating to EndoSure® Wireless AAA Pressure Measurement System, manufactured by CardioMEMS, Inc. (downloaded from: <http://www.cardiomems.com/content.asp?display=medical+mb&expand=ess>, on Nov. 30, 2010).
Wustmann, K. et al., "Effects of chronic baroreceptor stimulation on the autonomic cardiovascular regulation in patients with drug-resistant arterial hypertension," Hypertension 2009; 54;530-536.
International Preliminary Report on Patentability dated Aug. 3, 2010, which issued during the prosecution of Applicant's PCT/IL09/00117.
International Preliminary Report on Patentability dated Aug. 3, 2010, which issued during the prosecution of Applicant's PCT/IL09/00115.
International Preliminary Report on Patentability dated Jan. 24, 2007, which issued during the prosecution of Applicant's PCT/IL06/00856.
International Search Report and a Written Opinion both dated Jul. 13, 2009, which issued during the prosecution of Applicant's PCT/IL09/00117.
International Search Report and a Written Opinion both dated May 12, 2009, which issued during the prosecution of Applicant's PCT/IL09/00115.
International Search Report dated Dec. 19, 2011, which issued during the prosecution of Applicant's PCT/IL2011/000636.
International Search Report dated Jan. 24, 2007, which issued during the prosecution of Applicant's PCT/IL06/00856.
Office Action dated Aug. 9, 2011, which issued during the prosecution of U.S. Appl. No. 12/023,896.
Office Action dated Dec. 19, 2011, which issued during the prosecution of U.S. Appl. No. 11/995,904.
Office Action dated Mar. 15, 2012, which issued during the prosecution of U.S. Appl. No. 12/792,227.
Office Action dated Mar. 3, 2012, which issued during the prosecution of U.S. Appl. No. 12/023,896.
Office Action dated Nov. 18, 2009, which issued during the prosecution of U.S. Appl. No. 12/023,900.
U.S. Appl. No. 60/702,491, filed Jul. 25, 2005.
U.S. Appl. No. 60/721,728, filed Sep. 28, 2005.
Supplementary European Search Report dated Dec. 14, 2012 in connection with European Patent Application No. 06766171.
Office Action dated Apr. 25, 2013 issued during the prosecution of corresponding U.S. Appl. No. 11/995,904.
Office Action dated May 10, 2013 issued during the prosecution of corresponding U.S. Appl. No. 12/023,896.
Office Action dated Apr. 5, 2013 issued during the prosecution of corresponding U.S. Appl. No. 12/792,227.

\* cited by examiner

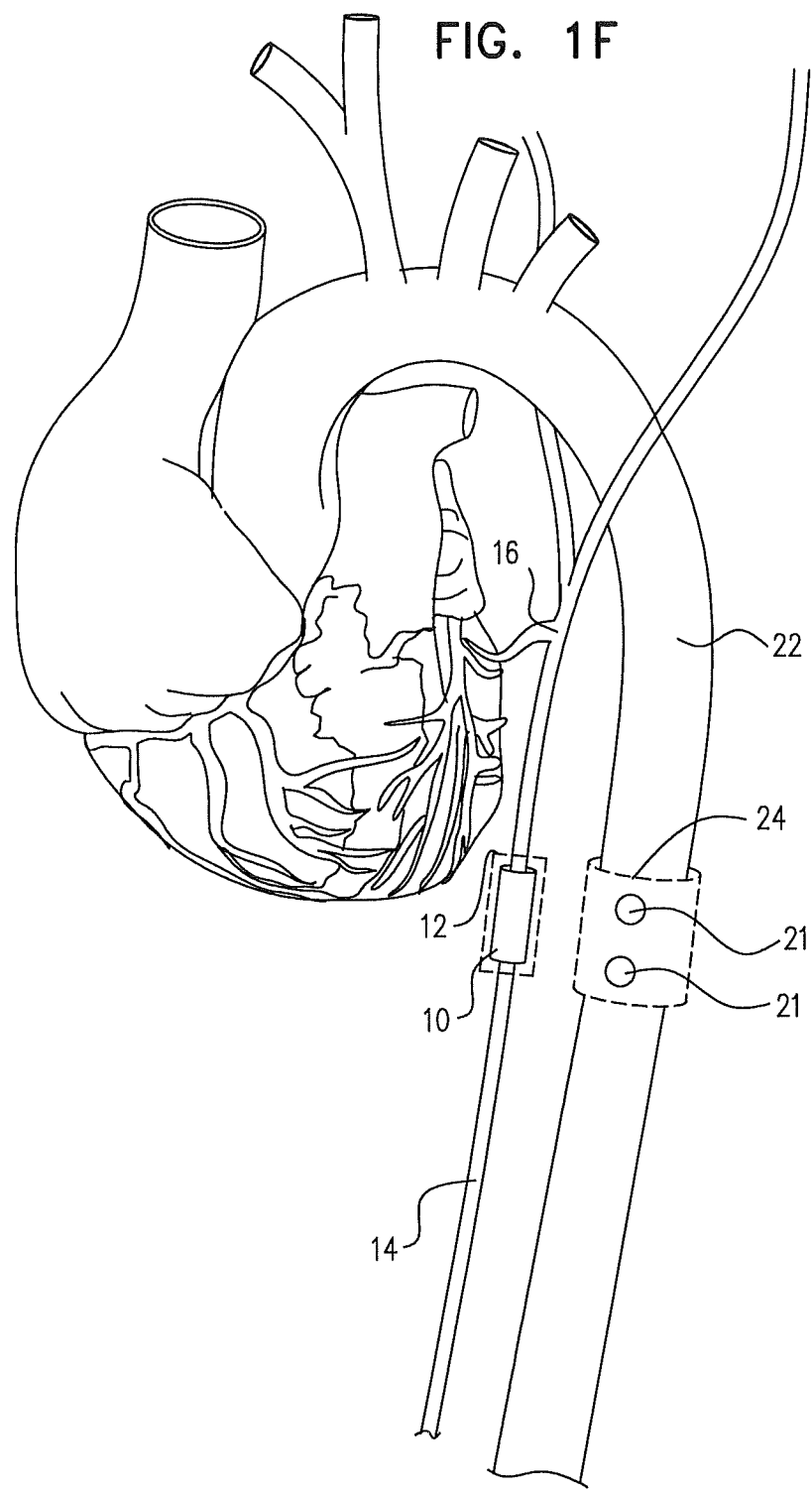

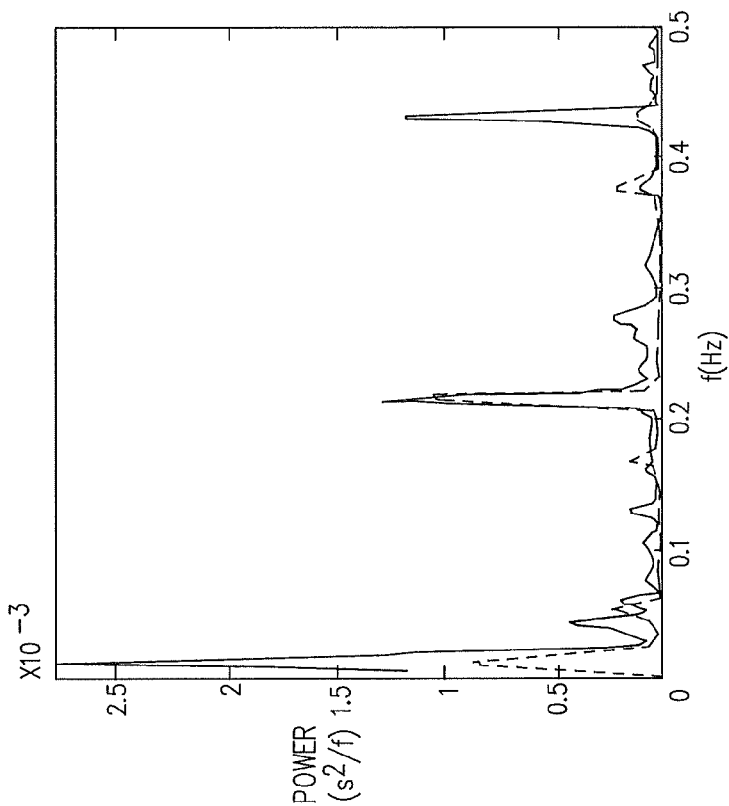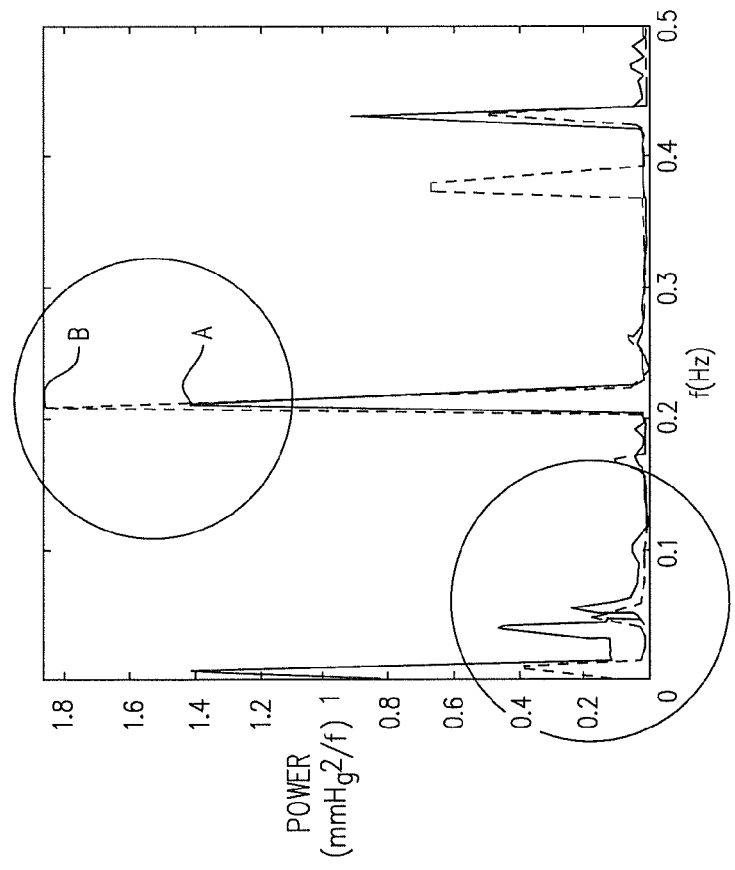

ACUTE MYOCARDIAL INFARCTION TREATMENT BY ELECTRICAL STIMULATION OF THE THORACIC AORTA

CROSS-REFERENCES TO RELATED APPLICATIONS

The present application is a continuation-in-part of U.S. Ser. No. 12/957,799 to Gross (published as U.S. 2011/0137370), filed Dec. 01, 2010, entitled "Thoracic aorta and vagus nerve stimulation," which is a continuation-in-part of U.S. Ser. No. 12/792,227 to Gross (published as U.S. 2010/0305392), filed Jun. 2, 2010, entitled "Thoracic aorta and vagus nerve stimulation," which claims the benefit of (a) U.S. Provisional Patent Application 61/183,319 to Reisner, filed Jun. 2, 2009, entitled "Thoracic aorta and vagus nerve stimulation," and (b) U.S. Provisional Patent Application 61/331,453 to Dagan, filed May 5, 2010, entitled "Thoracic aorta and vagus nerve stimulation."

FIELD OF EMBODIMENTS OF THE INVENTION

Some applications of the present invention generally relate to medical apparatus. Specifically, some applications of the present invention relate to apparatus and methods for treatment of acute myocardial infarction.

BACKGROUND

Acute myocardial infarction (AMI) is the result of interruption of blood supply to a part of the heart, causing heart cells to die. During AMI, damage is caused to the cardiac tissue by prolonged ischemia as well as due to injury during reperfusion.

Neurohormonal modulation, including inhibition of the sympathetic tone and activation of the parasympathetic tone to the heart, has been shown to have a protective effect on the cardiac tissue during ischemia and during reperfusion of the heart.

Beta blockers which inhibit the beta sympathetic tone are typically used in the treatment of AMI. There is evidence that intravenous beta blockers, administered acutely to treat AMI, reduce in-hospital mortality resulting from myocardial infarction, and are also useful in the control of the pain associated with AMI. Acute intravenous administration of beta blockers has been shown to improve the myocardial oxygen supply-demand relationship, decrease pain, reduce infarct size, and decrease the incidence of serious ventricular arrhythmias.

Typically, percutaneous coronary interventions are used to treat AMI. For example, procedures such as balloon dilatation and stent implantatibn are used to open a stenosis in the coronary arteries so as to re-perfuse the heart.

Reperfusion therapy is typically used in the treatment of ST elevation myocardial infarction (STEMI). Primary percutaneous coronary intervention (PCI) typically improves survival of STEMI. Ischemia and/or reperfusion injury is still an unresolved problem in STEMI treated by reperfusion therapy. Primary PCI can restore epicardial flow in 90-95% of patients, but 15-20% of patients do not achieve microvascular flow (known as the "no flow" phenomenon). Lack of microvascular perfusion after STEMI is the primary determinant of LV remodeling.

Heart failure is a condition in which a problem with the structure or function of the heart impairs its ability to supply sufficient blood flow to meet the body's needs. The condition impairs quality of life and is a leading cause of hospitalizations and mortality in the western world. Treatment of heart failure is typically aimed at removal of precipitating causes, prevention of deterioration in cardiac function, and control of congestive state.

Hypertension, or chronic high blood pressure, is an extremely prevalent medical condition, which can lead to strokes, heart attacks, and heart failure. There are a variety of treatments that are available for treating hypertension, including lifestyle changes, and medication.

SUMMARY OF EMBODIMENTS

For some applications of the present invention, a subject suffering from AMI is identified. The subject is treated by percutaneously placing at least one electrode inside the subject's aorta in contact with an aortic site, and electrically stimulating the aortic site. The aortic site is typically between the bifurcation of the aorta with the left subclavian artery and the bifurcation of the aorta with the fifth intercostal artery. For example, the aortic site may be (a) between the bifurcation of the aorta with the left subclavian artery and a location 4 cm downstream of the bifurcation, (b) between the bifurcation of the aorta with the left subclavian artery and the bifurcation of the aorta with the fourth intercostal artery, (c) between the bifurcation of the aorta with the left subclavian artery and the bifurcation of the aorta with the first intercostal artery, and/or (d) between the bifurcations of the aorta with the first and fifth intercostal arteries.

Typically, a plurality of electrodes are placed in contact with the aortic site. The electrical stimulation of the aortic site typically reduces afterload by suppressing the sympathetic tone of the heart and vasculature. Further typically, the stimulation of the aortic site reduces cardiac oxygen consumption, left ventricular workload, and/or coronary microvascular constriction, and/or induces cardiac microvascular dilation. For some applications, the electrical stimulation reduces the likelihood of a lethal arrhythmia occurring.

For some applications, total peripheral resistance of the subject is reduced, and/or aortic compliance is increased by applying the electrical stimulation. For some applications, the electrical stimulation causes a reduction in heart rate, left ventricular pressure, left ventricular oxygen consumption, left ventricular wall stress and/or left ventricular external work. For some applications, one or more of the aforementioned effects are caused by the electrical stimulation of the aortic site activating afferent aortic signals traveling via the left vagus nerve. For some applications, one or more of the aforementioned effects are achieved by the electrical stimulation of the aortic site suppressing the sympathetic tone and/or increasing the parasympathetic tone of the heart and vasculature.

Typically, the electrical stimulation is applied while a percutaneous coronary intervention is performed on the subject. For example, the electrical stimulation may be applied while balloon dilatation, and/or stent implantation are performed, in order to open a stenosis in the coronary arteries so as to re-perfuse the subject's heart. The electrical stimulation reduces afterload (in conjunction with causing additional effects, as described hereinabove), while the intervention is performed. For some applications, the electrical stimulation is applied for a period of time subsequent to the intervention having been performed, e.g., so as to protect the cardiac tissue by reducing afterload, cardiac oxygen consumption, left ventricular workload, and/or coronary microvascular constriction, and/or by inducing cardiac microvascular dilation, and/or by reducing reperfusion injury and apoptosis (in conjunction with causing additional effects, as described hereinabove), during reperfusion of the heart, subsequent to the intervention.

For some applications of the invention a subject suffering from congestive heart failure, diastolic heart failure, hypertension, and/or another condition is identified. The subject is typically treated by implanting at least one electrode on the subject's vagus nerve at a vagal site that is (i) between (a) the vagal bifurcation with the thoracic cardiac branch (i.e., the thoracic cardiac branch from the left recurrent laryngeal), and (b) the thoracic vagal branching into the esophageal plexus, and/or (ii) between (a) the upper junction of the left thoracic vagal trunk with the left subclavian artery and (b) the vagal bifurcation with the thoracic cardiac branch. Alternatively or additionally, at least one electrode is implanted in the vicinity of (i.e., inside, within the wall of, or outside of) the subject's aorta, at an aortic site that is typically as described hereinabove. Typically, a plurality of electrodes are implanted at the vagal site, and/or the aortic site. The subject is treated by driving a current into the electrode implantation site.

The effects of driving the current into the implantation site typically include ventricular and aortic pressure reduction, an increase in aortic compliance, a decrease in sympathetic tone, and/or an increase in parasympathetic tone. These effects are typically advantageous in treating heart failure.

There is therefore provided, in accordance with some applications of the present invention, a method, including:

identifying a subject as suffering from a condition selected from the group consisting of congestive heart failure, diastolic heart failure, acute myocardial infarction, and hypertension; and in response to the identifying:

placing an electrode on an aorta of the subject at an aortic site that is between a bifurcation of the aorta with a left subclavian artery of the subject and a bifurcation of the aorta with a fifth intercostal artery of the subject; and treating the subject by electrically stimulating the aortic site by driving a current into the aortic site, via the electrode.

For some applications, placing the electrode at the aortic site includes placing the electrode on a portion of the aorta that is adjacent to a portion of a vagus nerve of the subject that is between (a) a vagal bifurcation with a thoracic cardiac branch from a left recurrent laryngeal of the subject, and (b) thoracic vagal branching into the esophageal plexus of the subject.

For some applications, placing the electrode at the aortic site includes placing the electrode on a portion of the aorta that is adjacent to a portion of a vagus nerve of the subject that is between (a) an upper junction of the left thoracic vagal trunk with the left subclavian artery, and (b) a vagal bifurcation with a thoracic cardiac branch from a left recurrent laryngeal of the subject.

For some applications, placing the electrode at the aortic site includes placing the electrode at the aortic site that is between the bifurcation of the aorta with the left subclavian artery and a location 4 cm downstream of the bifurcation.

For some applications, treating the subject includes reducing ventricular pressure of the subject.

For some applications, treating the subject includes reducing aortic pressure of the subject.

For some applications, treating the subject includes reducing sympathetic tone of the subject.

For some applications, treating the subject includes increasing parasympathetic tone of the subject.

For some applications, treating the subject includes increasing parasympathetic tone of the subject and reducing sympathetic tone of the subject.

For some applications, treating the subject includes increasing aortic compliance of the subject.

For some applications, placing the electrode on the aorta includes assessing a response of the subject to placement of the electrode at a plurality of sites, and implanting the electrode at the aortic site in response to the assessing.

For some applications, placing the electrode at the aortic site includes implanting the electrode at the aortic site.

For some applications, identifying the subject as suffering from the condition includes identifying the subject as suffering from a condition selected from the group consisting of congestive heart failure, diastolic heart failure, and hypertension, and placing the electrode at the aortic site includes placing the electrode at the aortic site that is between the first and fifth intercostal arteries.

For some applications, placing the electrode at the aortic site includes placing the electrode at an aortic site that is between the bifurcation of the aorta with the left subclavian artery and a bifurcation of the aorta with a fourth intercostal artery of the subject.

For some applications, placing the electrode at the aortic site includes placing the electrode at an aortic site that is between the bifurcation of the aorta with the left subclavian artery and a bifurcation of the aorta with a first intercostal artery of the subject.

For some applications, the method further includes detecting an electrical signal at the aortic site, and deriving from the electrical signal a physiological parameter of the subject selected from the group consisting of: blood pressure of the subject and an ECG signal of the subject.

For some applications, detecting the electrical signal at the aortic site includes detecting the electrical signal using at least two electrodes that are disposed around a circumference of the aorta at the aortic site at a distance of more than 10 mm from one another.

For some applications, driving the current into the aortic site includes driving the current into the aortic site responsively to the detected electrical signal.

For some applications, deriving the physiological parameter includes deriving the subject's ECG signal, and driving the current into the aortic site includes driving the current into the aortic site in coordination with a QRS complex of the subject's ECG signal.

For some applications, treating the subject includes reducing a ratio of a low frequency component to a high frequency component of heart rate variability of the subject.

For some applications, the low frequency component is less than 0.05 Hz, and the high frequency component is between 0.15 and 0.35 Hz, and treating the subject includes reducing a ratio of the low frequency component of the heart rate variability that is less than 0.05 Hz, to the high frequency component of the heart rate variability that is between 0.15 and 0.35 Hz.

For some applications, treating the subject includes reducing a ratio of a low frequency component to a high frequency component of blood pressure variability of the subject.

For some applications, the low frequency component is less than 0.05 Hz, and the high frequency component is between 0.15 and 0.35 Hz, and treating the subject includes reducing a ratio of the low frequency component of the blood pressure variability that is less than 0.05 Hz, to the high frequency component of the blood pressure variability that is between 0.15 and 0.35 Hz.

For some applications, placing the electrode at the aortic site includes placing the electrode in contact with the aortic site of the subject's aorta by percutaneously inserting the electrode into the subject's body via a catheter, and the method further includes, subsequent to termination of the electrical stimulation, removing the electrode and the catheter from the subject's body.

For some applications, identifying the subject as suffering from the condition includes identifying the subject as suffering from acute myocardial infarction.

For some applications, the method further includes, in response to identifying the subject, performing a percutaneous coronary intervention, and electrically stimulating the aortic site includes driving the current into the aortic site, at least periodically, during the percutaneous coronary intervention, and for a period of time following the percutaneous coronary intervention.

For some applications, driving the current into the aortic site includes reducing afterload of the subject by driving the current into the aortic site via the electrode.

For some applications, driving the current into the aortic site includes reducing ventricular pressure of the subject by driving the current into the aortic site via the electrode.

For some applications, driving the current into the aortic site includes reducing aortic pressure of the subject by driving the current into the aortic site via the electrode.

For some applications, driving the current into the aortic site includes reducing sympathetic tone of the subject by driving the current into the aortic site via the electrode.

For some applications, driving the current into the aortic site includes increasing parasympathetic tone of the subject by driving the current into the aortic site via the electrode.

For some applications, driving the current into the aortic site includes reducing sympathetic tone and increasing parasympathetic tone of the subject by driving the current into the aortic site via the electrode.

For some applications, driving the current into the aortic site includes increasing aortic compliance of the subject by driving the current into the aortic site via the electrode.

For some applications, placing the electrode in contact with the aortic site includes assessing a response of the subject to placement of the electrode at a plurality of sites, and selecting one of the plurality of sites as the aortic site in response to the assessing.

For some applications, driving the current into the aortic site includes reducing ventricular work and oxygen consumption of the subject by driving the current into the aortic site via the electrode.

For some applications, driving the current into the aortic site includes increasing myocardial perfusion of the subject by driving the current into the aortic site via the electrode.

For some applications, driving the current into the aortic site includes reducing a likelihood of the myocardium being damaged due to ischemia by driving the current into the aortic site via the electrode.

For some applications, driving the current into the aortic site includes reducing a likelihood of the myocardium being damaged due to reperfusion injury by driving the current into the aortic site via the electrode.

For some applications, driving the current into the aortic site includes reducing a ratio of a low frequency component to a high frequency component of heart rate variability of the subject by driving the current into the aortic site via the electrode.

For some applications, the low frequency component is less than 0.05 Hz, and the high frequency component is between 0.15 and 0.35 Hz, and treating the subject includes reducing a ratio of the low frequency component of the heart rate variability that is less than 0.05 Hz, to the high frequency component of the heart rate variability that is between 0.15 and 0.35 Hz.

For some applications, driving the current into the aortic site includes reducing a ratio of a low frequency component to a high frequency component of blood pressure variability of the subject by driving the current into the aortic site via the electrode.

For some applications, the low frequency component is less than 0.05 Hz, the high frequency component is between 0.15 and 0.35 Hz, and treating the subject includes reducing a ratio of the low frequency component of the blood pressure variability that is less than 0.05 Hz, to the high frequency component of the blood pressure variability that is between 0.15 and 0.35 Hz.

There is further provided, in accordance with some applications of the present invention, a method, including:

identifying a subject as suffering from a condition selected from the group consisting of congestive heart failure, diastolic heart failure, acute myocardial infarction, and hypertension; and in response to the identifying:

placing an electrode on a vagus nerve of the subject at a vagal site that is between (a) an upper junction of the left thoracic vagal trunk with a left subclavian artery of the subject, and (b) thoracic vagal branching into the esophageal plexus of the subject; and treating the subject by electrically stimulating the aortic site by driving a current into the aortic site, via the electrode.

For some applications, placing the electrode on the vagus nerve includes placing the electrode on a portion of the vagus nerve that is between (a) a vagal bifurcation with a thoracic cardiac branch from the left recurrent laryngeal of the subject, and (b) the thoracic vagal branching into the esophageal plexus of the subject.

For some applications, placing the electrode on the vagus nerve includes placing the electrode on a portion of the vagus nerve that is between (a) the upper junction of the left thoracic vagal trunk with the left subclavian artery, and (b) a vagal bifurcation with a thoracic cardiac branch from the left recurrent laryngeal of the subject.

The present invention will be more fully understood from the following detailed description of embodiments thereof, taken together with the drawings, in which:

BRIEF DESCRIPTION OF THE DRAWINGS

FIG. 1F is a schematic illustration of electrode implantation sites, in accordance with some applications of the present invention;

FIG. 6 is a graph showing the effect of stimulating an aortic site of a pig on blood pressure variability of the pig, in accordance with some applications of the present invention;

FIG. 7 is a graph showing the effect of stimulating an aortic site of a pig on heart rate variability of the pig, in accordance with some applications of the present invention;

DETAILED DESCRIPTION OF EMBODIMENTS

Reference is now made to FIGS. 1A-E, which are schematic illustration of apparatus 20 for treatment of a subject suffering from AMI, in accordance with some applications of the present invention. For some applications of the invention, a subject suffering from AMI is identified. The subject is treated by percutaneously (e.g., transfemorally) placing at least one electrode 21 (typically, a plurality of electrodes) inside the subject's aorta 22 in contact with an aortic site 24, and electrically stimulating the aortic site, by driving a current into the aortic site. The current is typically driven into the aortic site by a control unit (e.g., a bedside work station) disposed outside the subject's body.

The electrical stimulation of the aortic site typically reduces afterload by suppressing the sympathetic tone. Further typically, the stimulation of the aortic site reduces cardiac oxygen consumption, left ventricular workload, and/or coronary microvascular constriction, and/or induces cardiac microvascular dilation. For some applications, the electrical stimulation reduces the likelihood of a lethal arrhythmia occurring. Typically, electrical stimulation of the aortic site leads to prevention of ventricular remodeling and/or reverse remodeling.

For some applications, total peripheral resistance of the subject is reduced, and/or aortic compliance is increased by applying the electrical stimulation. For some applications, during reperfusion of the heart, subsequent to the infarction, application of the electrical stimulation increases microvascular perfusion by causing vasodilation of the coronary arterioles, and/or protects ventricular myocytes from reperfusion injury (e.g., apoptosis and/or necrosis). For some applications, the electrical stimulation causes a reduction in heart rate, left ventricular pressure, aortic pressure, left ventricular oxygen consumption, left ventricular wall stress and/or left ventricular external work. For some applications, one or more of the aforementioned effects are caused by the electrical stimulation of the aortic site activating afferent aortic signals traveling via the left vagus nerve. For some applications, one or more of the aforementioned effects are achieved by the electrical stimulation of the aortic site suppressing the sympathetic tone and/or increasing the parasympathetic tone of the heart and vasculature.

Figure 1A:
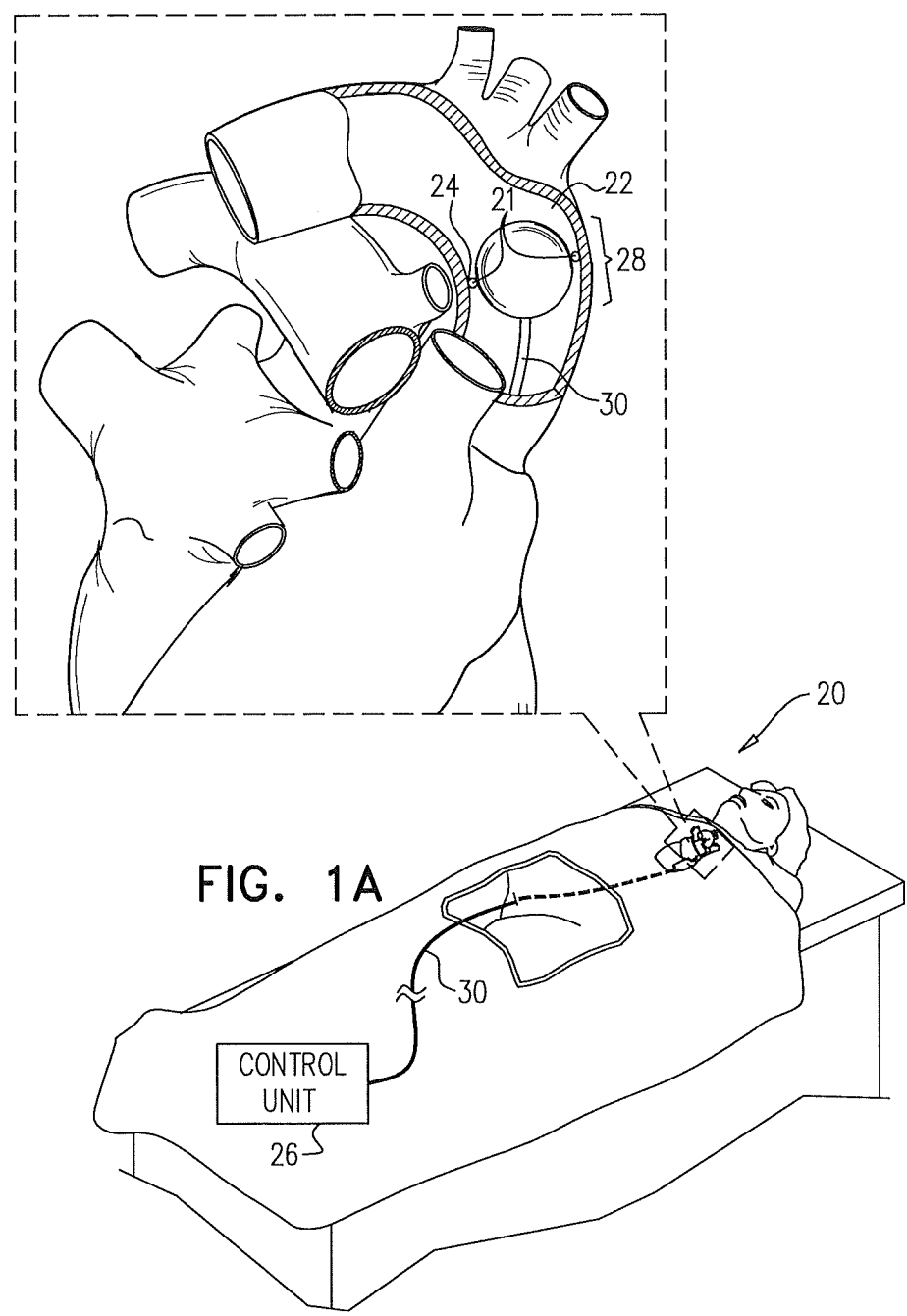
FIG. 1A is a schematic illustration of apparatus for acute treatment of a subject suffering from AMI, in accordance with some applications of the present invention.
Figure 1C:
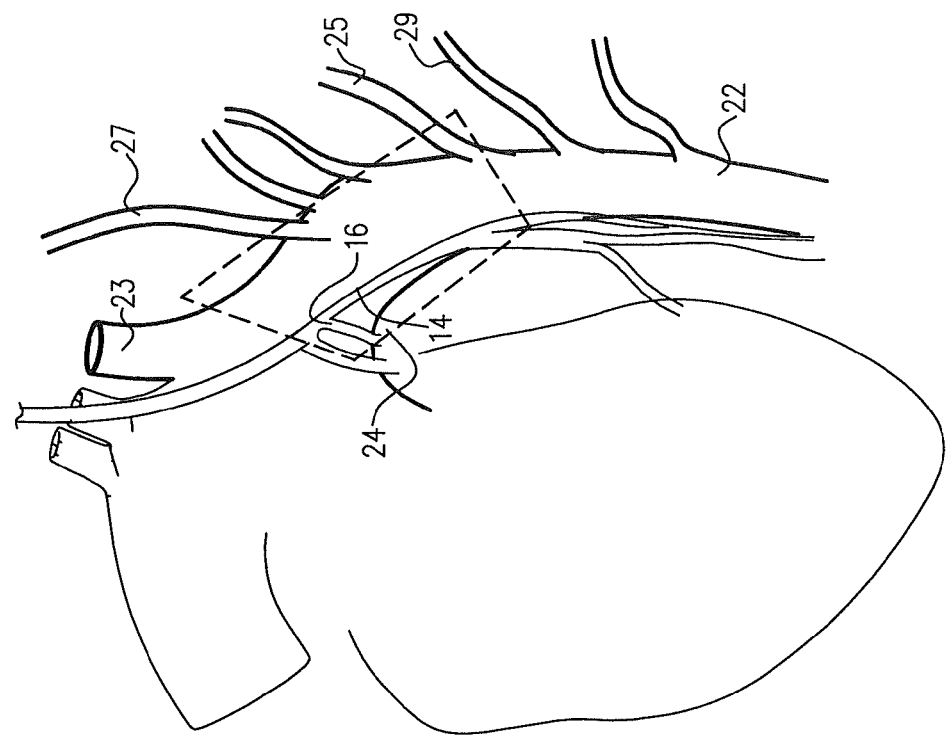
FIGS. 1B-E are schematic illustrations of an aortic site that is electrically stimulated, in accordance with some applications of the present invention.
Figure 1B:
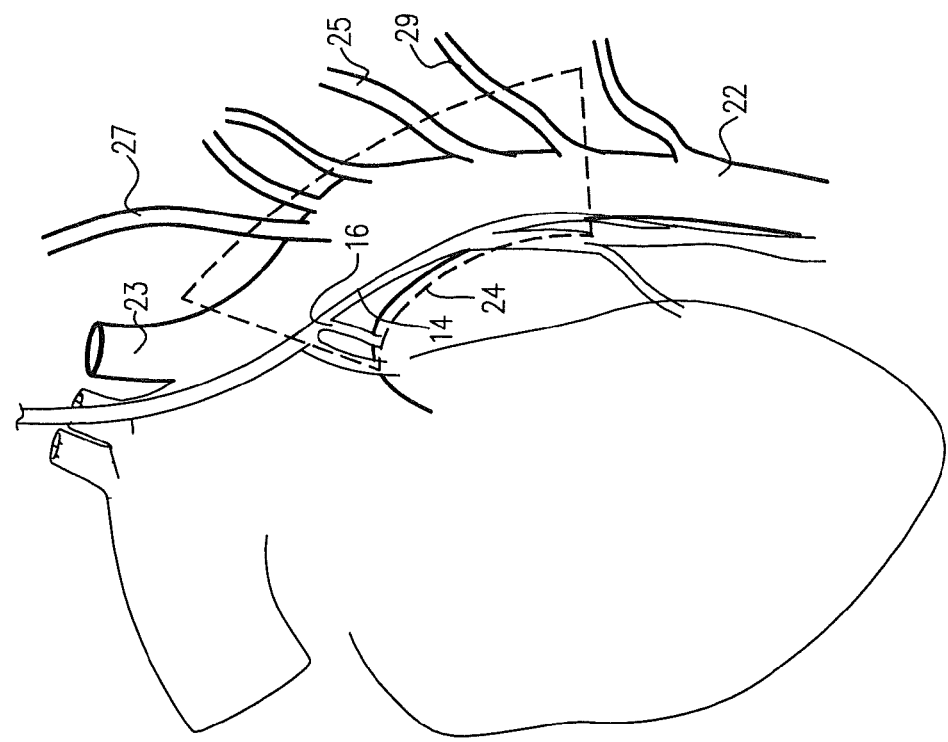
Figure 1D:
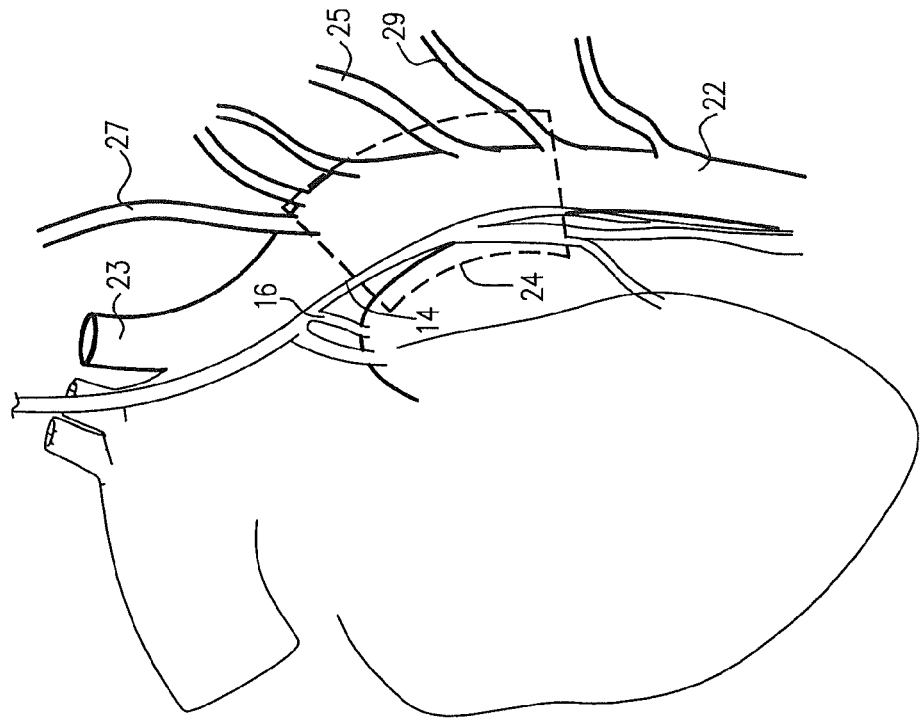
Figure 1E:
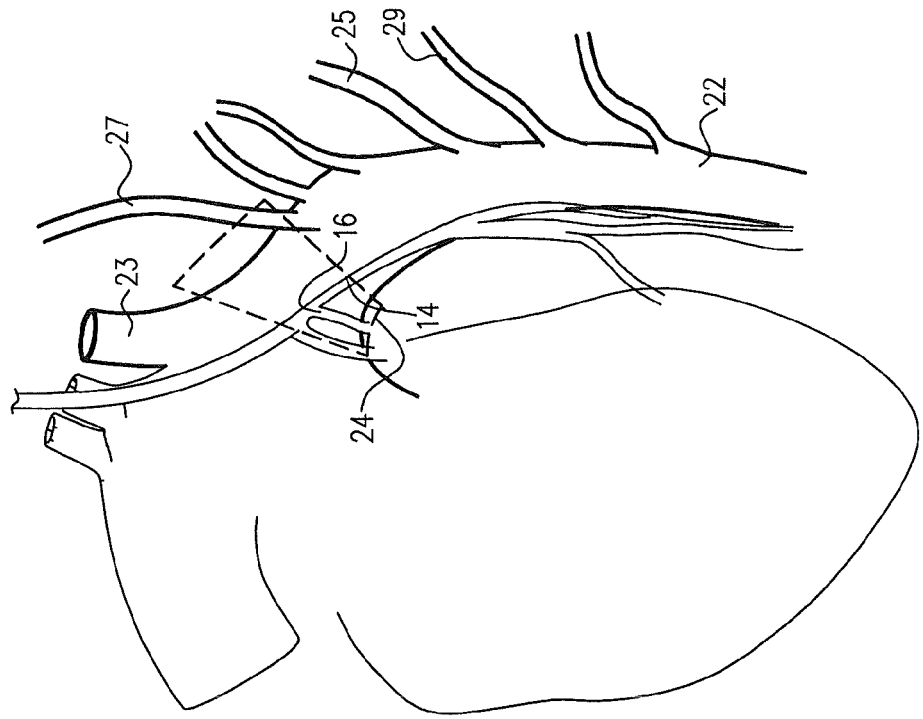
Figure 2:
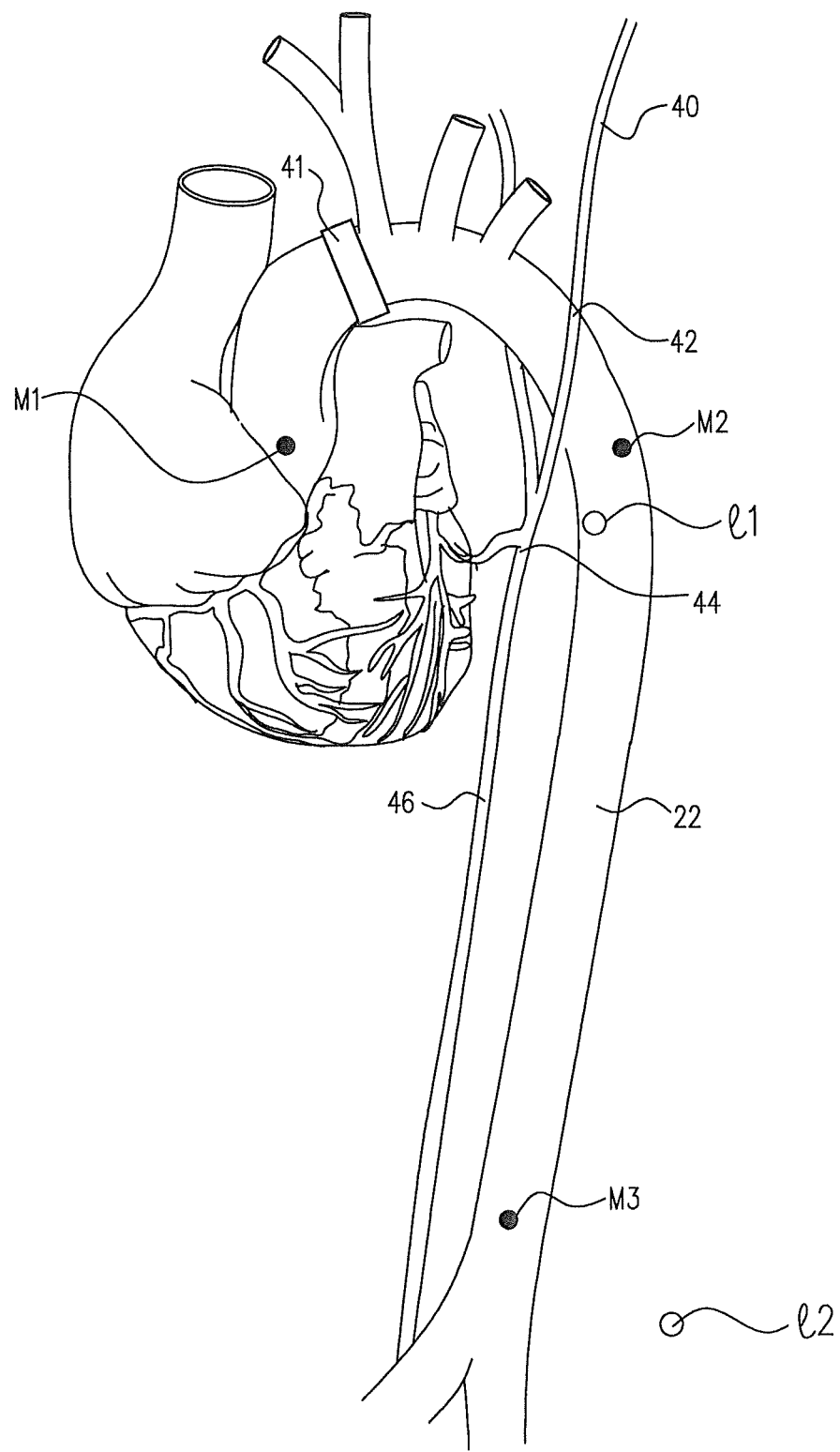
FIG. 2 is a schematic illustration of an experimental setup of an experiment conducted in accordance with some applications of the present invention.

Typically, the percutaneously-inserted electrode is placed in contact with an aortic site 24 that is between the bifurcation of aorta 22 with the left subclavian artery 23 and the bifurcation of the aorta with the fifth intercostal artery 29, the aortic site being as shown in FIG. 1B. For example the aortic site may be (a) between the bifurcation of the aorta with the left subclavian artery and a location 4 cm downstream of the bifurcation, (b) between the bifurcation of the aorta with the left subclavian artery and the bifurcation of the aorta with the fourth intercostal artery 25 (the aortic site being as shown in FIG. 1C), (c) between the bifurcation of the aorta with the left subclavian artery and the bifurcation of the aorta with the first intercostal artery 27 (the aortic site being as shown in FIG. 1D), and/or (d) between the bifurcations of the aorta with the first and fifth intercostal arteries (the aortic site being as shown in FIG. 1E). For some applications, the aortic site is adjacent to a portion of a vagus nerve 14 of the subject that is between (a) a vagal bifurcation 16 with a thoracic cardiac branch of the subject (i.e., the thoracic cardiac branch from the left recurrent laryngeal), and (b) thoracic vagal branching into the esophageal plexus of the subject. For some applications, the aortic site is adjacent to a portion of vagus nerve 14 that is slightly proximal to bifurcation 16, e.g., a portion of the vagus nerve between (a) the upper junction of the left thoracic vagal trunk with the left subclavian artery, and (b) bifurcation 16, such as a proximal thoracic location 42, as shown in FIG. 2.

Typically, a plurality of electrodes 21 are disposed on a distal portion 28 of a catheter 30 that is inserted into the aorta. The distal portion of the catheter is typically shaped so as to facilitate contact between the electrodes and the inner wall of the aorta. For example, the distal portion of the catheter may be looped, as described with reference to FIG. 8A, or an array of electrodes may be disposed around the distal portion of the catheter, as described with reference to FIG. 8B. Typically, the proximal end of the catheter is coupled to external control unit 26.

For some applications, subsequent to placing distal portion 28 of catheter 30 into the subject's aorta, electrode 21 is successively placed in contact with respective locations of the inner wall of the aorta, and the respective locations of the wall of the aorta are electrically stimulated via the electrode. Changes in physiological parameters of the subject resulting from the stimulation of the respective locations are measured. Responsively thereto, one of the locations is selected as the aortic site, and the electrode is placed in contact with the selected location for the remainder of the treatment or for a portion thereof.

For some applications, subsequent to electrode 21 being placed at aortic site 24, and commencement of the electrical stimulation via the electrode, physiological parameters of the subject, such as heart rate, and/or blood pressure, are measured. Responsively thereto, parameters of the electrical stimulation that is applied to the aortic site are adjusted.

For some applications, physiological parameters of the subject are measured by detecting an electrical signal at the aortic site, for example via the at least one electrode 21, and/or via a different set of electrodes (not shown), the electrical signal being interpreted as being indicative of a physiological parameter of the subject, for example, in accordance with the techniques described with reference to FIGS. 9-12, and 15A-B. For some applications, the subject's cardiac cycle is determined by deriving the subject's ECG from the electrical signal detected at the aorta, and the electrical stimulation is applied to the aortic site in coordination with the subject's cardiac cycle.

Typically, the electrical stimulation is applied (at least periodically) while a percutaneous coronary intervention is performed on the subject. For example, the electrical stimulation may be applied while balloon dilatation, and/or stent implantation are performed, in order to open a stenosis in the coronary arteries so as to re-perfuse the subject's heart. The electrical stimulation reduces afterload, cardiac oxygen consumption, left ventricular workload, and coronary microvascular constriction, and/or induces cardiac microvascular dilation (in conjunction with causing additional effects, as described hereinabove), while the intervention is performed.

For some applications, the electrical stimulation is applied for a period of time subsequent to the intervention having been performed, e.g., so as to protect the cardiac tissue by reducing afterload, cardiac oxygen consumption, left ventricular workload, and/or coronary microvascular constriction, and/or by inducing cardiac microvascular dilation, and/or by reducing reperfusion injury and apoptosis (in conjunction with causing additional effects, as described hereinabove), during reperfusion of the heart, subsequent to the intervention. Typically, the electrical stimulation is initiated during the intervention, and the stimulation continues for more than 1 hour and/or less than 72 hours (e.g., less than 24 hours). Subsequent to the termination of the electrical stimulation, catheter 30 and electrode 21 are removed from the subject's body (typically, immediately).

For some applications, the current is driven into the aortic site in coordination with the subject's cardiac cycle and/or respiratory cycle. For example, the subject's ECG may be detected, and the current may be driven into the electrode implantation site responsively to the detection of the QRS complex. Alternatively or additionally, the subject's blood pressure may be measured and the current may be driven responsively thereto. For some applications, the subject's ECG, and/or the subject's blood pressure is derived from an electrical signal detected at the aorta, using electrodes 21, or a different set of electrodes (not shown), in accordance with the techniques described with reference to FIGS. 9-12, and 15A-B. Alternatively, the current is driven independently of the subject's cardiac cycle and/or respiratory cycle.

For some applications, driving current into aortic site 24, via electrodes 21, dilates the aorta by increasing nitric oxide (NO) secretion by the wall of the aorta, and/or by increasing the secretion of another vasodilation mediator from the wall of the aorta. Typically, driving current into aortic site 24, via electrodes 21, inhibits the sympathetic system tone and enhances parasympathetic tone by activation of aortic afferent fibers. For some applications, driving current into aortic site 24, via electrodes 21, dilates the aorta by stimulating efferent nerve endings. For some applications, driving current into aortic site 24, via electrodes 21, dilates the aorta by direct electrical hyperpolarization of the vascular smooth muscle.

For some applications, driving current into aortic site, via electrode 21, activates afferent aortic signals traveling via the left vagus nerve thereby stimulating autonomic control centers in the central nervous system such as to enhance parasympathetic tone, thereby eliciting a parasympathetic response. For some applications, driving current into the aortic site generates an aortic response, as described hereinabove, in addition to generating the aforementioned vagal response. For some applications, driving the current into the aortic site stimulates autonomic control centers in the central nervous system, thereby inhibiting sympathetic tone, and inhibiting sympathetic signaling to the heart and periphery.

For some applications, driving current into the aortic site, via electrode 21 reduces a ratio of a low frequency component (e.g., less than 0.05 Hz) to a high frequency component (e.g., 0.15-0.35 Hz) of heart rate variability of the subject. For some applications, driving current into the aortic site, via electrode 21 reduces a ratio of a low frequency component (e.g., less than 0.05 Hz) to a high frequency component (e.g., 0.15-0.35 Hz) of blood pressure variability of the subject.

For some applications, the current has a frequency of between 5 Hz and 150 Hz, e.g., more than 100 Hz and/or less than 150 Hz. For some applications, the current has an amplitude of between 1 mA and 15 mA, e.g., between 2 mA and 3 mA. For some applications, a current having two pulses to 40 pulses, e.g., five pulses to thirty pulses (such as 20-30 pulses), per cardiac cycle, is driven into the aorta. In accordance with respective applications, the current is delivered continuously or intermittently. The current may thus be applied, for example: (a) as an endless train of pulses, or (b) during scheduled non-contiguous stimulation periods.

In a typical application, the current is driven as a symmetric rectangular biphasic pulse with 2 ms positive current and 2 ms negative current, at a frequency of approximately 125 Hz. Typically, the pulses are driven in coordination with the subject's QRS complex, and more than twenty pulses and/or less than forty pulses (e.g., approximately thirty pulses) are driven per cardiac cycle. Further typically, the pulses, cyclically, are driven into the aortic site during a stimulation period, and are not driven into the aortic site during rest periods between consecutive stimulation periods. For some applications, each stimulation period is more than 1 minute and/or less than three minutes, e.g., about two minutes. For some applications, each rest period is more than two minutes and/or less than four minutes, e.g., about three minutes.

Reference is now made to FIG. 1F, which is a schematic illustration of a vagal site 12 and aortic site 24 of a subject, in accordance with some applications of the present invention. The techniques described hereinabove with reference to FIG. 1A are typically used for treating a subject suffering from acute myocardial infarction, by percutaneously (e.g., transcatheterally) placing one or more aortic electrodes 21 at aortic site and electrically stimulating the aortic site by driving a current into the aortic site via the percutaneously-inserted aortic electrodes. Typically, in accordance with the techniques described with reference to FIG. 1A, subsequent to treatment of the subject having been terminated (e.g., within 24 hours of the treatment being terminated), the percutaneously-inserted electrodes are removed from the subject's body. In some alternative or additional applications of the present invention, at least one vagal electrode 10 is implanted at vagal site 12, and/or at least one aortic electrode 21 is implanted at aortic site 24, as shown in FIG. 1F. In FIG. 1F, vagus nerve 14 is shown separated from aorta 22 for illustrative purposes, although typically the vagus nerve is disposed adjacently to the aorta at aortic site 24, as shown in FIGS. 1B-E. In general, the anatomy shown in FIG. 1F is not drawn to scale, for illustrative purposes.

For some applications of the invention, a subject suffering from congestive heart failure, diastolic heart failure, and/or hypertension is identified. The subject is treated by implanting vagal electrode 10 on the subject's vagus nerve 14 at vagal site 12 that is between (a) the vagal bifurcation with thoracic cardiac branch 16 (i.e., the thoracic cardiac branch from the left recurrent laryngeal), and (b) the thoracic vagal branching into the esophageal plexus. For some applications, the vagal site is slightly proximal to bifurcation 16, for example, the vagal site may be between (a) the upper junction of the left thoracic vagal trunk with the left subclavian artery, and (b) bifurcation 16. As noted above, the anatomy shown in FIG. 1F is not drawn to scale, for illustrative purposes. It is further noted that the actual location of (a) the vagal bifurcation 16 with the thoracic cardiac branch with respect to (b) the aorta is typically as indicated in FIGS. 1B-E, and that FIG. 1F does not show the true relationship between locations of the aorta, the vagus nerve, and the thoracic cardiac branch.

Alternatively or additionally, one or more aortic electrodes 21 are implanted in the vicinity of (i.e., inside, outside, or, within the wall of) the subject's aorta 22, at aortic site 24. Aortic site 24 is typically as described hereinabove. Thus, aortic site 24 is typically between the bifurcation of aorta 22 with the left subclavian artery 23 and the bifurcation of the aorta with the fifth intercostal artery 29, the aortic site being as shown in FIG. 1B. For example, the aortic site may be (a) between the bifurcation of the aorta with the left subclavian artery and a location 4 cm downstream of the bifurcation, (b) between the bifurcation of the aorta with the left subclavian artery and the bifurcation of the aorta with the fourth intercostal artery 25 (the aortic site being as shown in FIG. 1C), (c) between the bifurcation of the aorta with the left subclavian artery and the bifurcation of the aorta with the first intercostal artery 27 (the aortic site being as shown in FIG. 1D), and/or (d) between the bifurcations of the aorta with the first and fifth intercostal arteries (the aortic site being as shown in FIG. 1E).

For some applications, aortic electrode 21 is implanted in the vicinity of a portion of the aorta that is adjacent to vagal site 12. For some applications, vagal electrode 10 is implanted on a portion of the vagus nerve that is adjacent to aortic site 24. The subject is treated by driving a current into one or more of the electrode implantation sites. The effects of driving the current into the implantation site typically include ventricular and aortic pressure reduction, an increase in aortic compliance, a decrease in sympathetic tone, an increase in parasympathetic tone, an increase in ejection fraction, a reduction in heart rate, a reduction in left ventricular wall stress, and/or a reduction in left ventricular myocardial oxygen consumption. For some applications, the electrical stimulation reduces the likelihood of a lethal arrhythmia occurring.

For some applications, an electrode is implanted inside a vein in the vicinity of vagal site 12. For example, the electrode may be implanted in the vena cava, the innominate vein, the subclavian vein, and/or the left or right internal jugular vein. A current is driven via the intravenously implanted electrode in order to stimulate the vagal site, in accordance with the techniques described herein. Alternatively or additionally, the electrode is implanted inside an artery of the subject in the vicinity of the vagal site other than (or in addition to) the aorta, such as the pulmonary artery and/or the carotid artery, and a current is driven via the electrode in order to stimulate the vagal site.

Typically, the lowering of the subject's blood pressure is achieved by driving the current into one or both of the implantation sites, without causing a substantial change in the subject's heart rate. For some applications, there is no substantial effect on the heart rate, because the current is driven into a site that is distal to the thoracic cardiac bifurcation (i.e., the bifurcation of the vagus nerve with the thoracic cardiac branch from the left recurrent laryngeal), and therefore does not have a substantial effect on efferent fibers that directly innervate the subject's heart. (For some applications, stimulating the vagus nerve distally to the thoracic cardiac bifurcation also has a heart rate lowering effect, but it is hypothesized by the inventors that this effect is mediated through central controls rather than direct efferent stimulation of the heart.) Alternatively, the current is driven into an aortic site that is adjacent to a portion of the vagus nerve that is proximal to the thoracic cardiac bifurcation.

For some applications, aortic electrodes 21 are disposed inside the aorta (i.e., electrodes 21 are intravascular electrodes). Alternatively or additionally, the electrodes are disposed in a wall of the aorta. Further alternatively or additionally, vagal electrode 10 is a cuff-electrode (or a different design) that is placed around, or in contact with, the vagus nerve. For some applications, electrode 10 and/or electrodes 21 are chronically implanted at sites 12 and/or 24. For some applications, aortic electrodes 21 are generally as shown in FIG. 8C.

For some applications, the current is driven into the electrode implantation site in coordination with the subject's cardiac cycle and/or respiratory cycle. For example, the subject's ECG may be detected, and the current may be driven into the electrode implantation site responsively to the detection of the QRS complex. Alternatively or additionally, the subject's blood pressure may be measured and the current may be driven responsively thereto. For some applications, the subject's ECG, and/or the subject's blood pressure is derived from an electrical signal detected at the aorta, using electrodes 21, or a different set of electrodes (not shown), in accordance with the techniques described with reference to FIGS. 9-12. Alternatively, the current is driven independently of the subject's cardiac cycle and/or respiratory cycle.

For some applications, driving current into aortic site 24, via electrodes 21, dilates the aorta by increasing nitric oxide (NO) secretion by the wall of the aorta, and/or by increasing the secretion of another vasodilation mediator from the wall of the aorta. Typically, driving current into aortic site 24, via electrodes 21, inhibits the sympathetic system tone and enhances parasympathetic tone by activation of aortic afferent fibers. For some applications, driving current into aortic site 24, via electrodes 21, dilates the aorta by stimulating efferent nerve ending. For some applications, driving current into aortic site 24, via electrodes 21, dilates the aorta by direct electrical hyperpolarization of the vascular smooth muscle.

For some applications, driving current into vagal site 12 activates afferent aortic signals traveling via the left vagus nerve thereby stimulating autonomic control centers in the central nervous system such as to enhance parasympathetic tone, thereby eliciting a parasympathetic response. For some applications, driving current into aortic site 24, via electrodes 21, has a similar effect on the vagus nerve (i.e., a vagal response), due to the proximity of aortic site 24 to vagal site 22, and/or due to baroreceptor fibers or nerve endings that are located at the aortic site. For some applications, driving current into the aortic site generates an aortic response, as described hereinabove, in addition to generating the aforementioned vagal response. For some applications, driving the current into the aortic site stimulates autonomic control centers in the central nervous system, thereby inhibiting sympathetic tone, and inhibiting sympathetic signaling to the heart and periphery.

For some applications, driving current into the aortic site, via electrode 21 reduces a ratio of a low frequency component (e.g., less than 0.05 Hz) to a high frequency component (e.g., 0.15-0.35 Hz) of heart rate variability of the subject. For some applications, driving current into the aortic site, via electrode 21 reduces a ratio of a low frequency component (e.g., less than 0.05 Hz) to a high frequency component (e.g., 0.15-0.35 Hz) of blood pressure variability of the subject.

For some applications, the current has a frequency of more than 5 Hz and/or less than 150 Hz, for example, between 5 Hz and 50 Hz. For some applications, the current has an amplitude of between 1 mA and 15 mA, e.g., between 2 mA and 3 mA. For some applications, a current having more than two pulses, and/or less than 40 pulses, for example, two pulses to eight pulses, or 30-40 pulses per cardiac cycle, is driven into the aorta. In accordance with respective applications, the current is delivered continuously or intermittently. The current may thus be applied, for example: (a) as an endless train of pulses, (b) during scheduled non-contiguous daily stimulation periods, or (c) during each of at least 24 consecutive hours.

For some applications, vagal site 12 is mechanically stimulated, for example, by mechanically stimulating the vagus nerve at the vagal site, and/or by mechanically stimulating aortic site 24, such that the vagal site also becomes stimulated. For some applications, the vagal site is stimulated using piezoelectric actuator terminals, an electrical motor, and/or an electroactive polymer actuator. For some applications, a balloon is placed in the vicinity of the vagal site, and is actuated to mechanically stimulate the vagus nerve using an external pump.

It is noted that some techniques are described herein for treating a subject suffering from congestive heart failure, diastolic heart failure, and/or hypertension, by implanting electrodes at aortic site 24 and/or at vagal site 12 and driving a current via the electrodes. However, the scope of the present invention includes treating a subject suffering from congestive heart failure, diastolic heart failure, and/or hypertension by percutaneously placing electrodes in contact with aortic site 24 and driving a current via the percutaneously-inserted electrodes, e.g., generally as described with reference to FIG. 1A.

Reference is now made to FIG. 2, which is a schematic illustration of an experimental setup of an experiment conducted in accordance with some applications of the present invention. Cuff electrodes were placed around a pig's vagus nerve at the following four locations:

(1) cervical location 40;
(2) proximal thoracic location 42 which is proximal to (i.e., closer to the CNS than) where the vagus has crossed the aorta;
(3) medial thoracic location 44, 1-2 cm below the aortic arch as the vagus nerve runs alongside the descending aorta, and just distal to (i.e., further from the CNS than) the thoracic cardiac branch bifurcation with the vagus nerve (i.e., the bifurcation of the vagus nerve with the thoracic cardiac branch from the left recurrent laryngeal); and
(4) distal thoracic location 46, just distal to (i.e., in a downstream direction along the aorta from) the crossing of the azygos vein with the aorta, and approximately 3 cm distal to (i.e., further from the CNS than) the thoracic cardiac branch bifurcation with the vagus nerve (i.e., the bifurcation of the vagus nerve with the thoracic cardiac branch from the left recurrent laryngeal).

Reference electrodes e1 and e2 were placed inside the pig's body, as shown in FIG. 2. Three Millar high fidelity pressure transducers M1, M2, and M3 were placed, respectively, in the left ventricle, the proximal descending aorta and in the abdominal aorta proximal to the iliac bifurcation. A Transonic flow transducer 41 was positioned around the aortic root. Three minutes of continuous electrical stimulation was applied to each of the sites. Respective sites of the pig's vagus were stimulated in accordance with the parameters provided in Table 1.

TABLE 1

| Stimulation parameters | | | | | |
|---|---|---|---|---|---|
| Active pole | Ref. pole | amplitude [mA] | freq [Hz] | pulse width | stimulation duration |
| 46 Distal | e1 | 5 | 50 | 1-1 ms* | 3 min |
| 44 Medial | e1 | 5 | 50 | 1-1 ms | 3 min |
| 42 Proximal | e1 | 5 | 50 | 1-1 ms | 3 min |
| 40 Cervical | e2 | 5 | 50 | 1-1 ms | 3 min |

*i.e., a 1 ms positive pulse, followed by a 1 ms symmetric negative pulse

Figure 3:
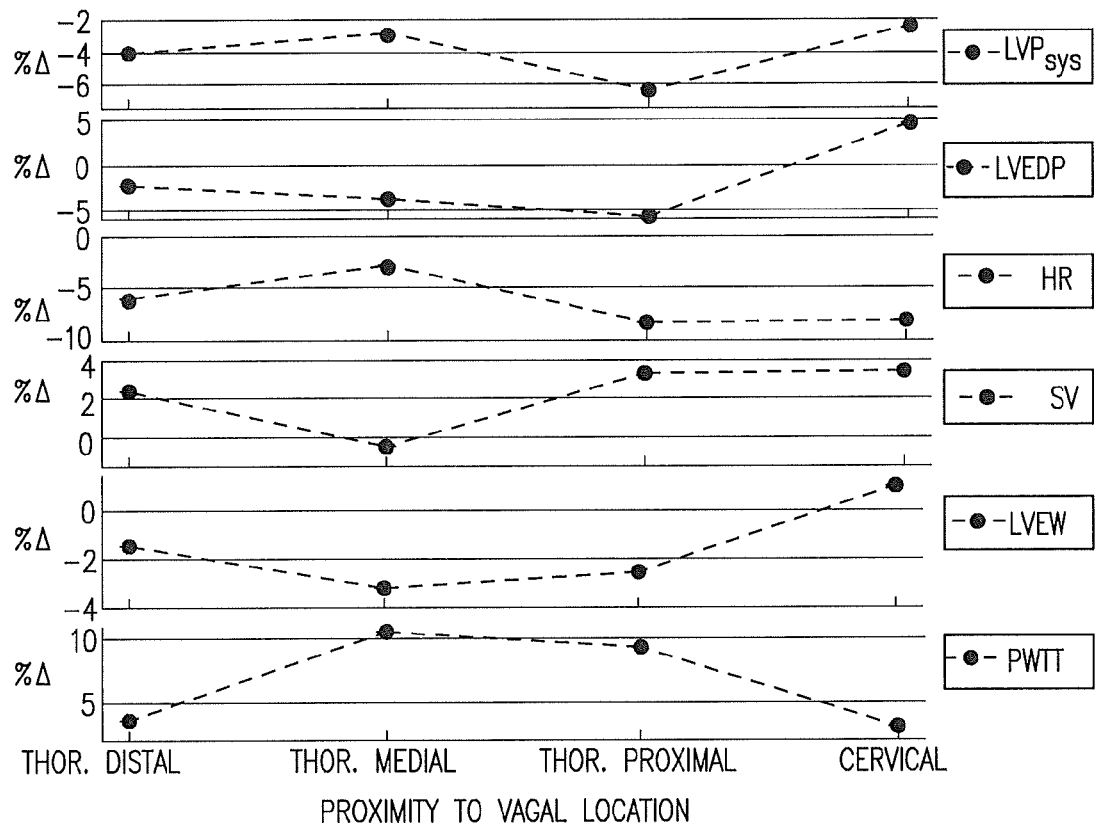
FIG. 3 is a set of graphs showing the results of stimulating a subject's vagus nerve on several physiological parameters of the subject, as determined in the experiment conducted in accordance with some applications of the present invention.

Reference is now made to FIG. 3, which is a set of graphs showing the results of stimulating the pig's vagus on several physiological parameters of pig, as determined in the experiment described with reference to FIG. 2. The following parameters were determined.

LVPsys—Average systolic left ventricular pressure during the ejection phase (aortic valve opening to aortic valve closure).
LVEDP—Left ventricular end diastolic pressure.
HR—Heart rate.
SV—Stroke volume as measured in the aortic root.
LVEW—Left ventricular external work. The integral of the product of left ventricular pressure and aortic flow during ejection phase.
PWTT—Pulse wave travel time between two measuring points along the aorta. PWTT is correlated to the square root of the diameter of the aorta divided by stiffness. Hence, increased PWTT (decreased pulse wave velocity) is associated with decreased aortic wall tonus.

The numeric values shown in the graphs of FIG. 3 represent the average of each parameter, for respective stimulation sites, during the entire stimulation regime.

The following observations can be made regarding the graphs shown in FIG. 3:

Electrical stimulation at all locations induced a reduction of average systolic left ventricular pressure during the ejection phase and heart rate. The systolic left ventricular pressure reduction was maximal in the proximal site and minimal in the cervical site.
The left ventricular end diastolic pressure was reduced in the thoracic sites and increased in the cervical site.
Heart rate reduction was maximal in the proximal thoracic and cervical sites.
Stroke volume did not exhibit a clear trend, as the medial thoracic site yielded a slight decrease and the other sites resulted in 2-4% increase.
Left ventricular external work, which is related to cardiac consumption, was lower as a result of stimulation of the thoracic sites and higher while stimulating the cervical site.
Stimulation at all of the sites resulted in an increase in pulse wave travel time (i.e., a decrease in aortic tonus). Stimulation of the proximal and medial sites resulted in the largest pulse delay along the aorta.

Figure 4:
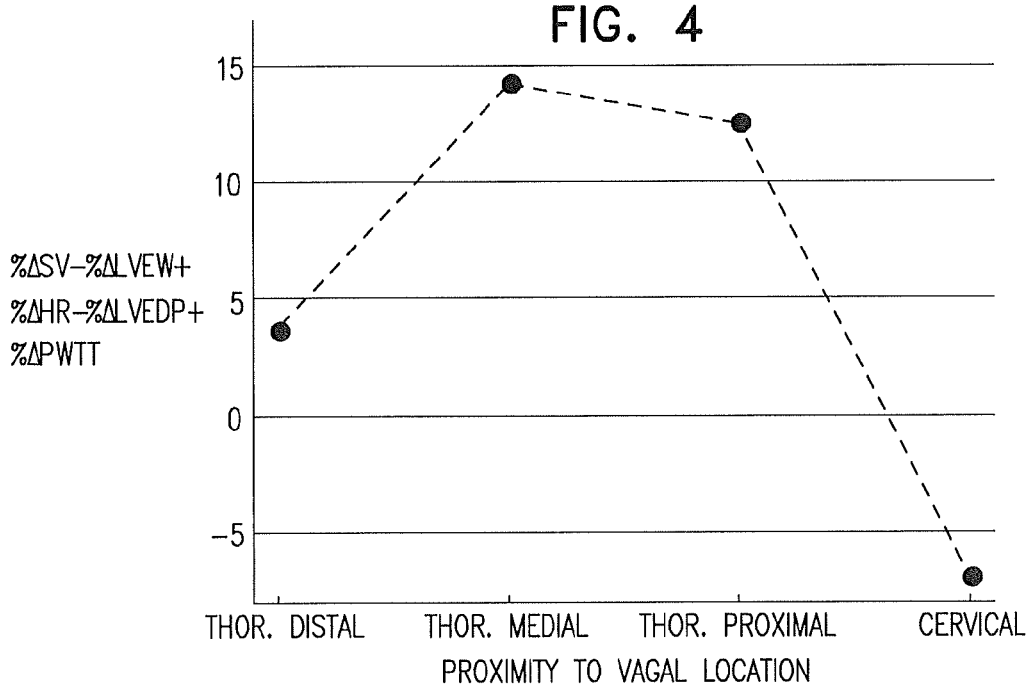
FIG. 4 is a graph showing a composite result of stimulating the subject's vagus nerve, as determined in the experiment conducted in accordance with some applications of the present invention.

Reference is now made to FIG. 4, which is a graph showing a composite result of stimulating the pig's vagus, as determined in this experiment. In order to evaluate each of the stimulation sites with one parameter, a first order scoring function was applied. The percentage change in each of the parameters shown in the graph of FIG. 3 was added to the total score, and its sign was determined according to the presumed beneficial direction. Left ventricular external work and left ventricular end diastolic pressure, which are targeted to be reduced (when treating patients suffering from hypertension, for example), were added with negative signs. Pulse wave travel time and stroke volume were added with positive signs. The heart rate reduction was also assigned a positive score.

The function results are plotted in the graph shown in FIG. 4. It may be observed that all of the thoracic sites achieved positive scores, and, in particular, the proximal thoracic and medial thoracic sites scored highly. Thus, for some applications, a vagal site is selected that is (i) between (a) the vagal bifurcation with thoracic cardiac branch 16 (i.e., the thoracic cardiac branch from the left recurrent laryngeal), and (b) the thoracic vagal branching into the esophageal plexus, and/or (ii) between (a) the upper junction of the left thoracic vagal trunk with the left subclavian artery and (b) bifurcation 16. The cervical vagal site achieved an overall negative score, since, although it had a positive effect on heart rate (i.e., heart rate reduction), its effect on pressure and work reduction was non-beneficial across the entire stimulation regime.

Figure 5:
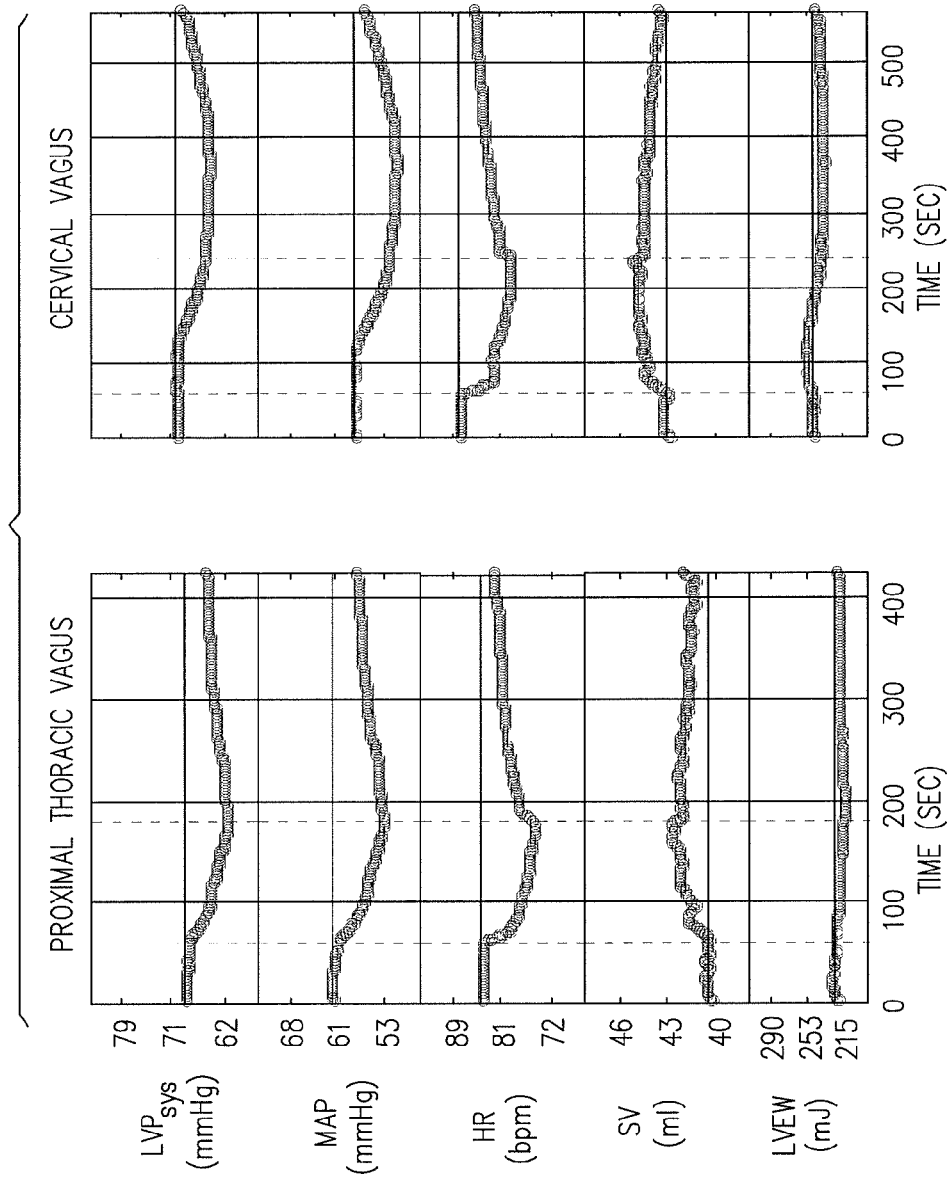
FIG. 5 is a graph showing the dynamic response of a subject to the stimulation of the subject's vagus nerve, as determined in the experiment conducted in accordance with some applications of the present invention.

Reference is now made to FIG. 5, which is a graph showing the dynamic response of the pig to the stimulation of the pig's vagus nerve, as determined in this experiment. The dynamic response to stimulation of the proximal thoracic and the cervical sites is shown in FIG. 5. The beginnings and ends of the stimulation period are marked with dashed vertical lines, at approximately 60 sec and 180 sec on the proximal thoracic vagus graph, and 60 sec and 230 sec on the cervical vagus graph. Heart rate response in both cases was immediate and continued for the duration of the stimulation period. Similarly, there was stroke volume elevation for the duration of the stimulation, due to stimulation at both sites. The pressure and left ventricular external work responses were not similar, however. The proximal thoracic site generated almost immediate pressure and work reduction. In the cervical site, the pressure reduction appeared only late in stimulation (possibly, as a secondary indirect phenomenon), and the left ventricular external work parameter responded with initial increases that were present across most of the stimulation regime.

In view of the results presented herein, it is hypothesized by the inventors of the present application that, as compared to stimulation of the cervical vagus, stimulation of thoracic vagal sites (e.g., by stimulating aortic site 24), as described herein, results in (a) a greater overall desired response with respect to ventricular and aortic blood pressure reduction and decreased aortic tonus, and (b) a more rapid response time to the stimulation. The inventors further hypothesize that placing electrodes on an aortic site (e.g., by implanting the electrodes at the aortic site, and/or by percutaneously placing the electrodes in contact with the aortic site) that is as described hereinabove and driving a current into the aortic site via the electrodes, will generate a similar response to the response of the pig to the placement of electrodes at the proximal, medial and distal vagal sites and the driving of a current through the electrodes, in the experiment described herein.

The inventors further hypothesize that stimulating a subject's aorta at the sites specified herein is beneficial for treating the subject, such that the subject's (a) ventricular blood pressure, aortic blood pressure, and/or tonus of the aorta, and/or arterioles (e.g., coronary arterioles) is reduced, without causing (b) a substantial reduction in the subject's heart rate.

Reference is now made to FIG. 6, which is a graph showing the effect of stimulating an aortic site of a pig on blood pressure variability of the pig, in accordance with some applications of the present invention. Two aortic electrodes were placed inside the pig's aorta at an aortic site between the bifurcations of the descending thoracic aorta with the first and fifth intercostal arteries. To generate the graph shown in FIG. 6, the baseline blood pressure variability of the pig was measured (while the electrodes were not applying current to the aortic site). The baseline blood pressure variability is denoted in the graph by the solid curve. The curve was generated by collecting the baseline data for seven minutes. Subsequently, the electrodes were driven to drive a current into the aortic site having the following parameters: amplitude 10 mA, frequency 125 Hz, and symmetric biphasic rectangular pulses with 2 ms positive current and 2 ms negative current. Blood pressure was measured during the stimulation period. The dotted curve in FIG. 6 shows the blood pressure variability based on seven minutes of the measured blood pressure during the stimulation period.

It may be observed that the effect of the stimulation on the blood pressure variability was to decrease the low frequency components of the blood pressure (those less than 0.15 Hz, e.g., less than 0.05 Hz) and to increase the high frequency components (those in the range of 0.15-0.35 Hz). For example, the frequency component at about 0.21 Hz increases from peak A to peak B, as shown. Thus, the stimulation at the aortic site caused a decrease in the ratio of low frequency components to the high frequency components ("the LF:HF ratio"). In accordance with an article entitled, "Sympathovagal balance is major determinant of short-term blood pressure variability in healthy subjects," by Laitinen, Am J Physiol Heart Circ Physiol 276:1245-1252, 1999, which is incorporated herein by reference, a decrease in the LF:HF ratio is indicative of inhibition of sympathetic activity and/or an increase of parasympathetic activity. This is because the low frequency components of the blood pressure variability are indicative of sympathetic activity, and the high frequency components are indicative of parasympathetic vagal activity. This experiment, therefore, not only shows a decrease in the LF:HF ratio, but also, inhibition of sympathetic activity and increase of parasympathetic activity.

Reference is now made to FIG. 7, which is a graph showing the effect of stimulating an aortic site of a pig on heart rate variability of the pig, in accordance with some applications of the present invention. It is noted that the pig used to generate the results shown in FIG. 7 was a different pig from the pig used to generate the results shown in FIG. 6.

Two aortic electrodes were placed inside the pig's aorta at an aortic site between the bifurcations of the descending thoracic aorta with the first and fifth intercostal arteries. To generate the graph shown in FIG. 7, the baseline heart rate variability of the pig was measured, while the electrodes were not applying current to the aortic site. The baseline heart variability is denoted in the graph by the solid curve. The curve was generated by collecting the baseline data for seven minutes. The electrodes were driven to drive a current into the aortic site having the following parameters: amplitude 10 mA, frequency 125 Hz, and symmetric biphasic rectangular pulses with 2 ms positive current and 2 ms negative current. The heart rate of the pig was measured during the stimulation period. The dotted curve in FIG. 7 shows the heart rate variability based on seven minutes of the measured blood pressure during the stimulation period.

It may be observed that the effect of the stimulation on the heart rate variability was to decrease the low frequency components of the heart rate variability (those less than 0.15 Hz, e.g., less than 0.5 Hz). Thus, the stimulation at the aortic site caused a decrease in the ratio of low frequency components to the high frequency components ("the LF:HF ratio"). In accordance with a technique described in "Effects of chronic baroreceptor stimulation on the autonomic cardiovascular regulation in patients with drug-resistant arterial hypertension," by Wustmann, Hypertension 2009;54;530-536, which is incorporated herein by reference, a decrease in the LF:HF ratio of heart rate variability is indicative of inhibition of sympathetic activity and/or an increase of parasympathetic vagal activity. In this experiment, a decrease in sympathetic activity is seen with respect to the baseline level of sympathetic activity.

It is noted that although it may be observed in FIG. 7 that stimulation of the pig caused a decrease in frequency components of the heart rate variability above 0.4 Hz, such components are not indicative of parasympathetic activity. Only the high frequency components up to around 0.35 Hz indicate parasympathetic activity, in accordance with the article, "Heart rate variability," Eur Heart J, Vol. 17, March 1996, and, in particular, FIG. 4 thereof. Although some frequency components in the range of 0.15-0.35 Hz were decreased (e.g., at about 0.23 Hz), the decrease in these frequency components was small relative to the decrease in the low frequency components (e.g., at about 0.02 Hz). Therefore, the overall effect of the stimulation was to cause a decrease in the LF:HF ratio.

In accordance with the results shown in FIGS. 6 and 7, for some applications, a subject suffering from AMI is treated by placing electrodes at an aortic site as described herein (e.g., by percutaneously placing the electrodes in contact with the aortic site), and driving a current into the aortic site via the electrodes. Alternatively, a subject suffering from a different condition (e.g., a subject suffering from congestive heart failure, diastolic heart failure, and/or hypertension, as described hereinabove) is treated by placing electrodes at an aortic site as described herein (e.g., by implanting the electrodes at the aortic site, and/or by percutaneously placing the electrodes in contact with the aortic site), and driving a current into the aortic site via the electrodes. Parasympathetic activity of the subject is increased and/or sympathetic activity of the subject is decreased by driving the current into the site.

Figure 8A:
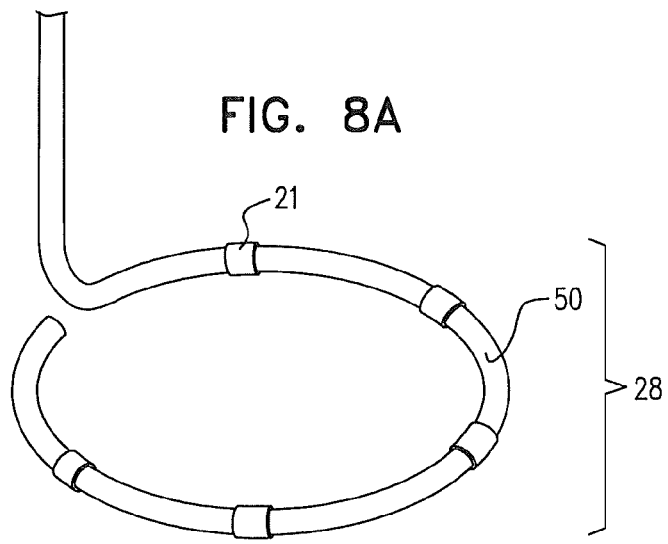
FIGS. 8A-C are schematic illustrations of electrode configurations that are used, in accordance with some applications of the present invention.
Figure 8B:
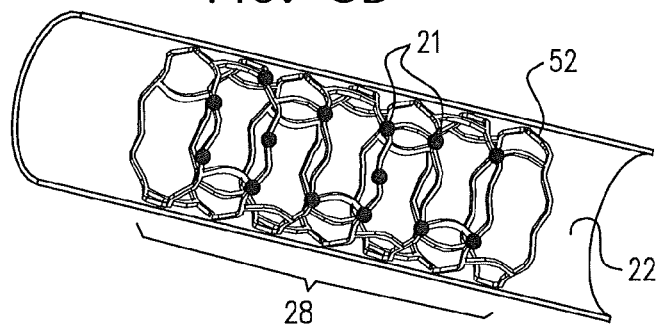
Figure 8C:
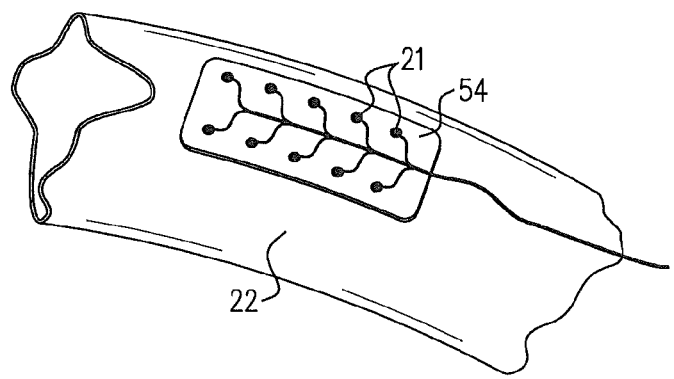

Reference is now made to FIGS. 8A-C, which are schematic illustrations of respective electrode configurations that are used for stimulating aortic site 24 of a subject, in accordance with some applications of the present invention. The electrode configurations shown in FIGS. 8A-B are typically used for applications in which electrodes 21 are temporarily placed in contact with the aortic site, e.g., by being inserted percutaneously. The electrode configuration shown in FIG. 8C is typically used for applications in which the electrodes are implanted at aortic site 24.

As described hereinabove, for some applications, electrodes 21 are disposed on a distal portion 28 of catheter 30. For some applications, the distal portion of the catheter is a loop 50, as shown in FIG. 8A. The loop is percutaneously (e.g., transfemorally) placed inside the subject's aorta at the aortic site, such that the electrodes contact the intravascular surface of the aorta at the aortic site. When the electrodes have been placed in contact with the intravascular surface of the aorta, current is driven into the aorta via the electrodes, in accordance with the methods described hereinabove. For example, the LASSO 2515 Variable Circular Mapping Catheter, manufactured by Biosense Webster, may be used for loop 50.

For some applications, one or more electrodes 21 are disposed in an array on a mesh or a stent 52, the mesh or stent comprising distal portion 28 of the catheter, as shown in FIG. 8B. (For some applications, mesh or stent 52 is placed at the aortic site by being advanced through a lumen of the catheter, and the mesh or the stent effectively acts as the distal portion of the catheter when the mesh or the stent is pushed out of the distal end of the catheter.) The distal portion of the catheter is percutaneously (e.g., transfemorally) placed inside the subject's aorta at the aortic site, such that the aortic electrodes contact the intravascular surface of the aorta at the aortic site.

When the electrodes have been placed in contact with the intravascular surface of the aorta, current is driven into the aorta via the electrodes, in accordance with the methods described hereinabove.

Typically, the electrode configurations shown in FIGS. 8A-B are used to stimulate the aortic site during an acute treatment of the subject, e.g., to acutely treat AMI, as described hereinabove.

For some applications, electrodes 21 are disposed on a patch 54, as shown in FIG. 8C. The patch is implanted on an outer surface of the aorta at aortic site 24, such that the electrodes are in contact with the aortic site. For example, the patch may be sutured to the outer surface of the aorta at the aortic site. When the electrodes have been placed in contact with the extravascular surface of the aorta, current is driven into the aorta via the electrodes, in accordance with the methods described hereinabove.

Figure 9:
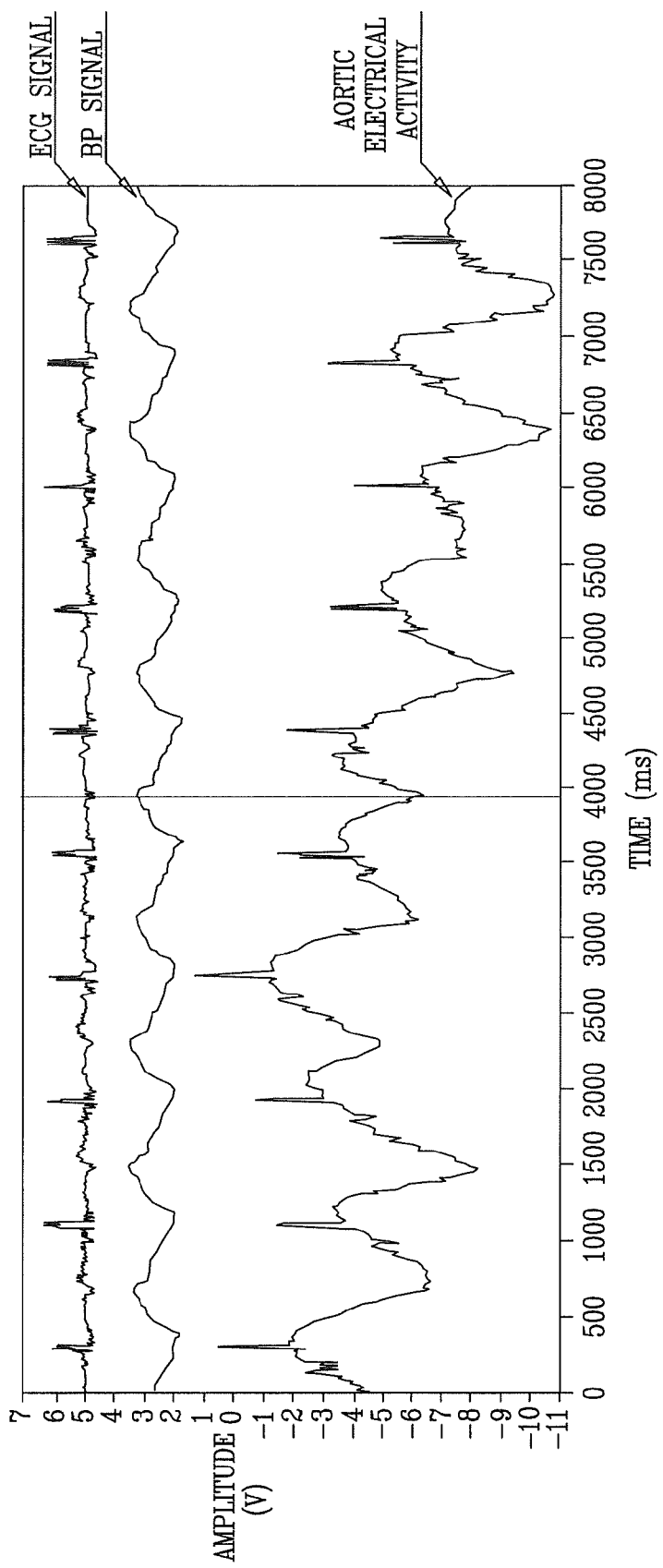
FIG. 9 is a plot of an aortic voltage signal recorded in an aorta of a pig, in an experiment conducted in accordance with some applications of the present invention.

Reference is now made to FIG. 9, which is a graph of aortic electrical activity recorded in an aorta of a pig, in an experiment conducted in accordance with some applications of the present invention. Ten electrodes were placed in an aorta of a pig close to the aortic valve, and the voltage within the aorta was recorded via four of the ten electrodes. The graph shows the variation of the voltage within the aorta plotted against time. In addition, and concurrently, the pig's ECG and blood pressure were measured. The graph additionally shows the concurrent ECG and blood pressure measurements, which were respectively recorded with an external ECG electrode and with an intra-aortic blood pressure sensor.

Based upon the data in FIG. 9 and in other experiments carried out by the inventors, the inventors have identified relationships between the cardiac cycle and the voltage recorded in the aorta. For example:

(1) There is a sharp peak in the aortic voltage about 50-100 ms before the onset of the aortic pressure rise due to systole. For example, at 2000 ms there is an onset of the pressure rise, and about 70 ms before this onset there is a sharp peak in the aortic voltage.

(2) Shortly before the onset of the aortic pressure decline due to diastole, the aortic voltage reaches a minimum. For example, there is a solid vertical line through the graph at about 3950 ms, at which point, the aortic voltage is at a local minimum. At about 4000 ms, diastole begins.

(3) A signal component in the measured aortic voltage corresponds to, and appears quite similar to, the R-wave recorded with an external ECG electrode, shown in the top trace. For example, the spike in the aortic voltage signal at 6000 ms corresponds to the R-wave in the ECG signal at 6000 ms.

Thus, the inventors have found that important mechanical events (onset of aortic pressure rise and aortic pressure decline) and electrical events (the R-wave) can be identified by aortic sensing.

Figure 10:
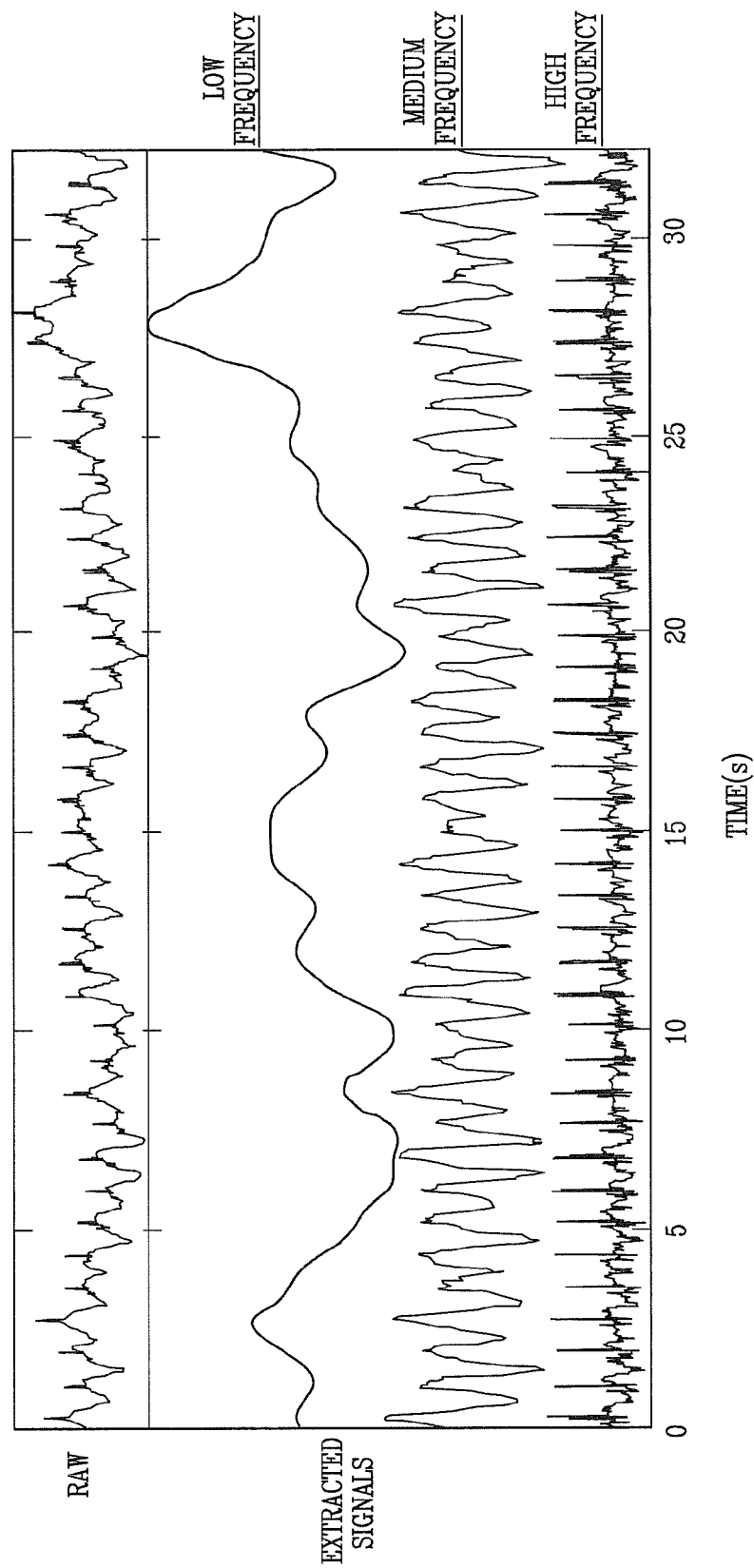
FIG. 10 is a plot showing frequency components of the aortic voltage signal of FIG. 9, as extracted from the raw aortic voltage signal in accordance with some applications of the present invention.

Reference is now made to FIG. 10, which is a plot showing frequency components extracted from the raw aortic voltage signal of FIG. 9, in accordance with some applications of the present invention. The aortic voltage signal was separated into three frequency components, a low-frequency component, a medium-frequency component, and a high-frequency component.

Figure 11:
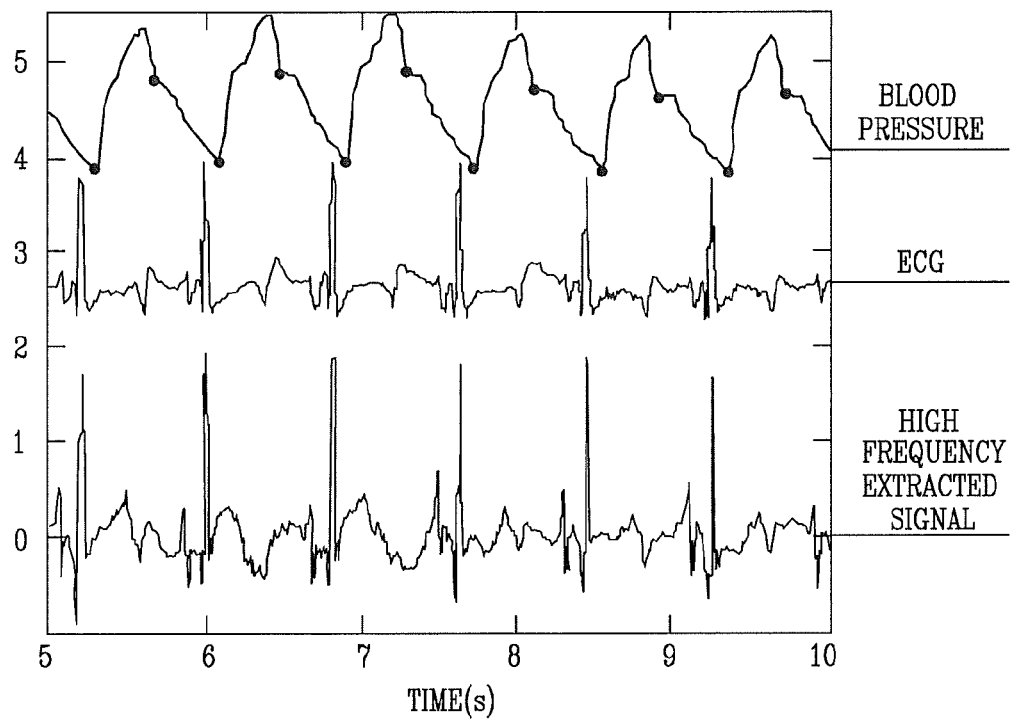
FIG. 11 is a plot comparing a frequency component of the aortic voltage signal of FIG. 9 to the pig's ECG and blood pressure signals, in accordance with some applications of the present invention.

Reference is now made to FIG. 11, which shows the high frequency component of the aortic voltage signal plotted together with an ECG recorded by the external electrode and the recorded blood pressure. It was observed by the inventors that the high frequency component has a similar pattern to the ECG signal, as can be seen in FIG. 11. Furthermore, there is a relationship between the occurrence of systole and diastole (which are indicated by the dots on the blood pressure plot), and the plot of the high frequency signal. As such, for some applications of the invention, an ECG signal of a subject is detected by sensing an electrical parameter in the subject's aorta. For some applications, a subject's ECG signal is detected by sensing electrical activity of another non-coronary blood vessel of the subject. For example, a sensing electrode placed in the vicinity of a non-coronary artery other than the aorta may be used to detect the subject's ECG signal.

As described hereinabove, for some applications, physiological parameters of the subject are measured, in order to facilitate selection of aortic site 24. Alternatively or additionally, subsequent to electrode 21 being placed at aortic site 24, and commencement of the electrical stimulation via the electrode, physiological parameters of the subject are measured, and responsively thereto, parameters of the electrical stimulation that is applied to the aortic site are adjusted. For some applications, physiological parameters of the subject are measured by detecting an electrical signal at the aortic site, via electrode 21. The electrical signal at the aortic site is interpreted as being indicative of a physiological parameter of the subject, in accordance with the data shown in FIGS. 9-11.

For some applications, the subject's cardiac cycle is determined by deriving the subject's ECG from the electrical signal detected at the aorta, and the electrical stimulation is applied to the aortic site in coordination with the subject's cardiac cycle. For example, a train of pulses (e.g., a train of more than 20 pulses, and/or less than 40 pulses, such as 25-30 pulses) may be delivered to the aortic site, responsively to the detection of the subject's QRS complex.

Figure 12:
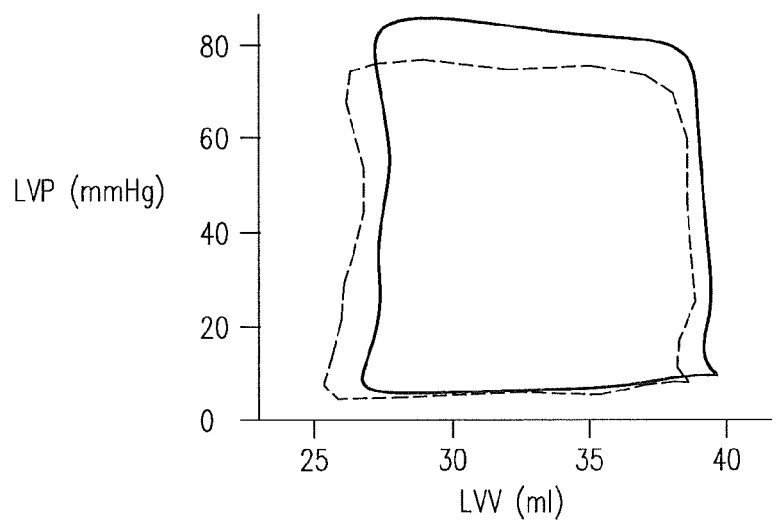
FIGS. 12-14, 15A and 15B are graphs showing experimental data that were obtained in experiments conducted in accordance with some applications of the present invention.
Figure 13:
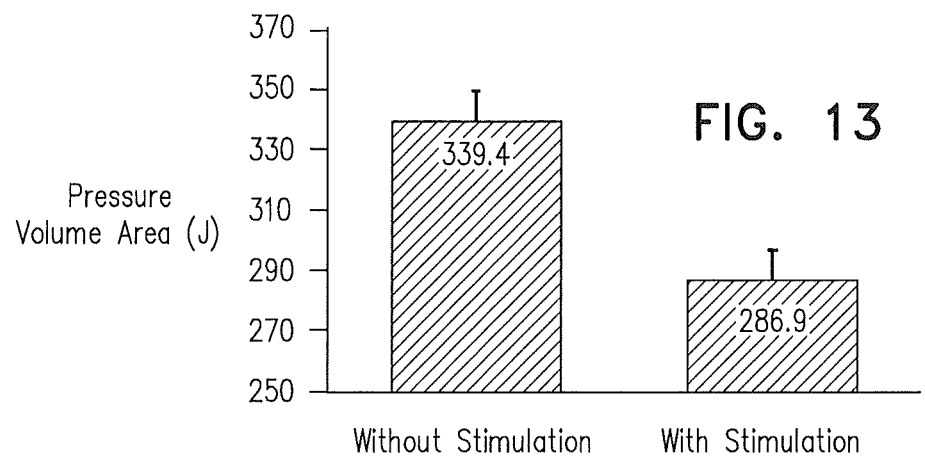
Figure 14:
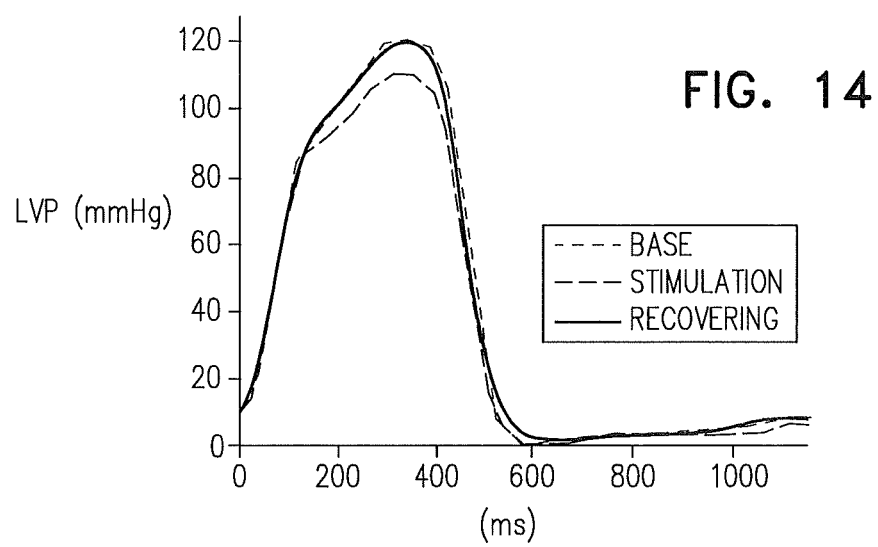

Reference is now made to FIGS. 12-14, which are graphs showing experimental data that were obtained in experiments conducted in accordance with some applications of the present invention.

The graph shown in FIG. 12 shows the left ventricular pressure versus left ventricular volume curve of a dog with induced heart failure. The left ventricular pressure and left ventricular volume of the dog were measured using a Millar pressure-volume (P-V) conductance catheter system, in accordance with techniques described in Angeli et al., Cardiovasc Drugs Ther (2010) 24:409-420. The solid curve in the graph shown in FIG. 12 is the dog's left ventricular pressure versus left ventricular volume curve as measured over a period of two to three minutes, before the dog's aorta was electrically stimulated. The dog's aorta was electrically stimulated at an aortic site between the bifurcation of the aorta with the left subclavian artery and the bifurcation of the aorta with the first intercostal artery. The dog was stimulated acutely using the LASSO 2515 Variable Circular Mapping Catheter with 10 mA, 125 Hz, symmetric biphasic rectangular pulses with 2 ms positive current and 2 ms negative current.

The dashed curve shown in FIG. 12 is the dog's left ventricular pressure versus left ventricular volume curve as measured while the dog was being stimulated for a period of two minutes. Subsequent to the termination of the electrical stimulation at the aortic site, the dog's left ventricular pressure versus volume curve returned to the pre-stimulation curve, i.e., the solid curve shown in FIG. 12.

A shift in a left ventricular pressure versus left ventricular volume curve toward the x and y axes (i.e., downward and to the left) is indicative of afterload reduction, as described in David Kass, Eur Heart J. 1992 Nov; 13 Suppl E:57-64, which is incorporated herein by reference. Thus, the shift of the left ventricular pressure versus volume curve of the dog downward and to the left during the electrical stimulation of the aortic site is indicative of the fact that the acute electrical stimulation of the dog's aorta resulted in a reduction in afterload during the stimulation period. These data indicate that acutely stimulating an aortic site in accordance with techniques described herein, will cause a reduction in a subject's afterload at least during the stimulation period. Thus, in accordance with some applications of the present invention, the aortic site of a subject suffering from a myocardial infarction is stimulated during, and/or for a period subsequent to, a percutaneous coronary intervention being applied to the subject, so as to reduce the subject's afterload during the application of the stimulation. Alternatively or additionally, the aortic site of a subject suffering from a different condition is stimulated acutely, so as to reduce the subject's afterload during the application of the stimulation.

The bar chart shown in FIG. 13 shows the mean left ventricular pressure-volume area of a group of six dogs. All of the dogs were suffering from heart failure, and had had electrodes implanted at an aortic site between the bifurcation of the aorta with the left subclavian artery and the bifurcation of the aorta with the first intercostal artery. A Millar pressure-volume (P-V) conductance catheter system was placed in the left ventricle of each of the dogs to facilitate measurement of left ventricular pressure and left ventricular volume of the dogs. An inflatable balloon catheter was placed in the inferior vena cava of each of the dogs.

Baseline PVA curves for the dogs were recorded, while electrical stimulation was not being applied to the aortic sites of the dogs. The baseline curves were recorded for each of the dogs by inflating the inferior-vena-cava balloon for several seconds and then deflating the balloon. The left ventricular pressure and volume of the dogs was measured during the inflation and the subsequent deflation, using the Millar pressure-volume (P-V) conductance catheter system, in accordance with techniques described in Steendijk et al., European Heart Journal (2004) 6 (Supplement D), D35-D42, which is incorporated herein by reference. The average pressure volume area of the dogs' baseline PVA curves was determined and is plotted as the left bar of the bar chart shown in FIG. 13.

Subsequently, electrical stimulation of the aortic sites of the dogs was initiated, and it was determined that, as a result of the electrical stimulation, the dogs had undergone a blood pressure decrease that had stabilized. Subsequent to the stabilization of the blood pressure decrease, stimulation PVA curves for the dogs were recorded, while the electrical stimulation continued to be applied to the aortic sites of the dogs. The stimulation curves were recorded for each of the dogs by inflating the inferior-vena-cava balloon for several seconds and then deflating the balloon. The left ventricular pressure and volume of the dog was measured during the inflation and the subsequent deflation, using the Millar pressure-volume (P-V) conductance catheter system. The average pressure volume area of the dogs' stimulation PVA curves was determined and is plotted as the right bar of the bar chart shown in FIG. 13.

There is a highly linear correlation between the pressure volume area of a subject's left ventricle and myocardial oxygen consumption per heartbeat, as described in Suga et al., Am J Physiol. 1981 Jan; 240(1):H39-44, which is incorporated herein by reference. This relationship holds true under a variety of loading and contractile conditions. This estimation of myocardial oxygen consumption is used to study the coupling of mechanical work and the energy requirement of the heart in various disease states, such as diabetes, ventricular hypertrophy and heart failure. Myocardial oxygen consumption is also used in the calculation of cardiac efficiency, which is the ratio of cardiac stroke work to myocardial oxygen consumption. As shown in FIG. 13, acute stimulation of the aortic site of the heart failure dogs using techniques described herein substantially reduced the left ventricular pressure volume area of the dogs relative to the baseline pressure volume area of the dogs. The data had a P-value of 0.05. The data shown in FIG. 13 indicate that acutely stimulating an aortic site, in accordance with techniques described herein, will cause a reduction in a subject's myocardial oxygen consumption at least during the stimulation period. Thus, in accordance with some applications of the present invention, the aortic site of a subject suffering from a myocardial infarction is stimulated during, and/or for a period subsequent to, a percutaneous coronary intervention being applied to the subject, so as to reduce the subject's myocardial oxygen consumption during the application of the stimulation. Alternatively or additionally, the aortic site of a subject suffering from a different condition is stimulated acutely, so as to reduce the subject's myocardial oxygen consumption during the application of the stimulation.

FIG. 14 is a graph showing left ventricular pressure as measured in a post-myocardial infarction human subject that generally suffered from heart failure. The subject was treated by acutely stimulating an aortic site of the subject between the bifurcation of the aorta with the left subclavian artery and a location 4 cm downstream of the bifurcation. Electrical stimulation was applied to the aortic site for a stimulation period of two minutes, via electrodes that were disposed on a LASSO 2515 Variable Circular Mapping Catheter, manufactured by Biosense Webster. The subject's mean left ventricular pressure waveform over the course of a cardiac cycle is shown in FIG. 14, as measured before stimulation (base), during stimulation, and two minutes subsequent to the stimulation (recovering). As shown in FIG. 14, during application of the stimulation, the subject's left ventricular pressure was reduced. The subject's left ventricular pressure waveform returned to having a generally similar shape to the baseline shape subsequent to the termination of the electrical stimulation. These data indicate that acutely stimulating an aortic site in accordance with techniques described herein, will cause a reduction in a subject's left ventricular pressure at least during the stimulation period. Thus, in accordance with some applications of the present invention, the aortic site of a subject suffering from a myocardial infarction is stimulated during, and/or for a period subsequent to, a percutaneous coronary intervention being applied to the subject, so as to reduce the subject's left ventricular pressure during the application of the stimulation. Alternatively or additionally, the aortic site of a subject suffering from a different condition is stimulated acutely, so as to reduce the subject's left ventricular pressure during the application of the stimulation.

Figure 15A:
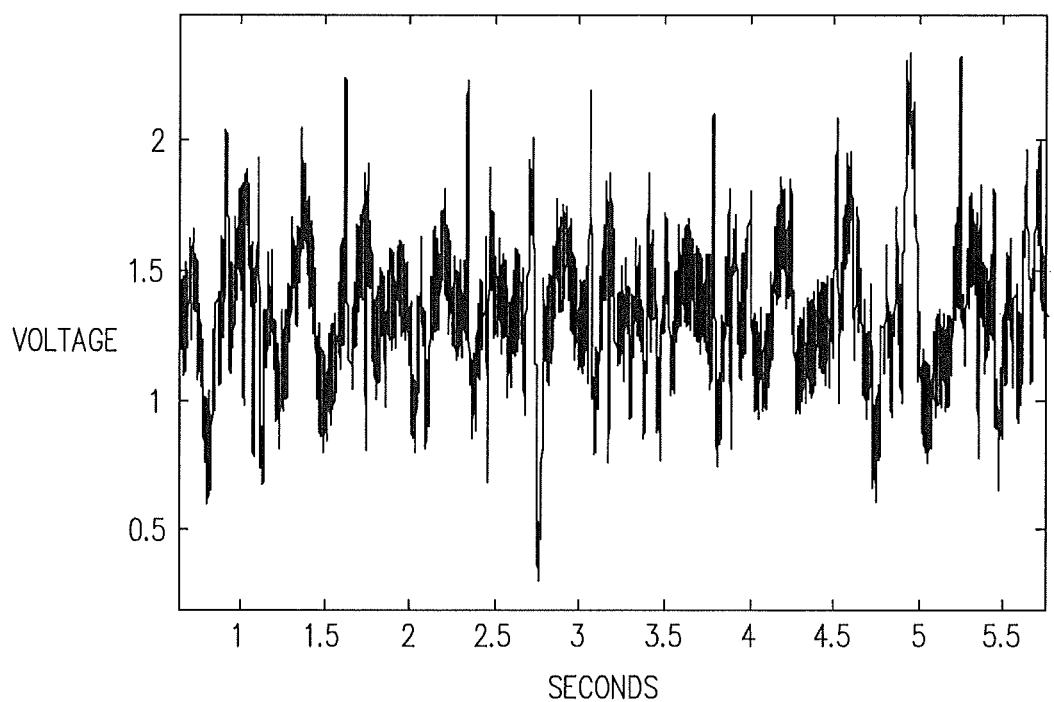
Figure 15B:
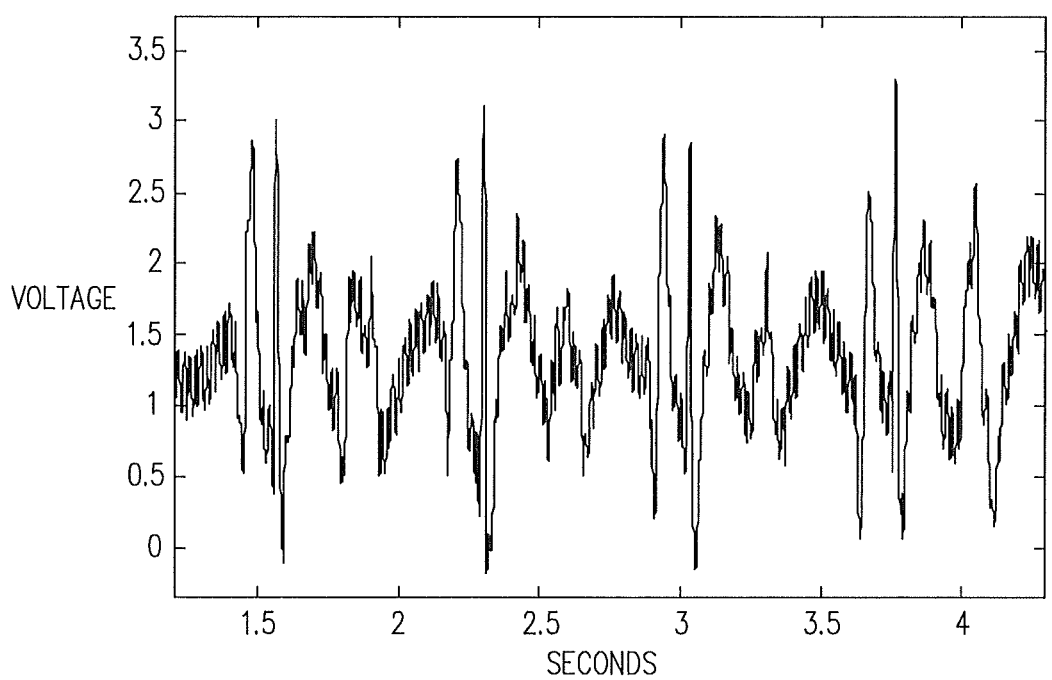

Reference is now made to FIGS. 15A-B, which are graphs showing experimental data that were obtained in experiments conducted in accordance with some applications of the present invention. The graphs shown in FIGS. 15A-B show unfiltered electrical signals recorded from a pig aorta at an aortic site between the bifurcation of the aorta with the left subclavian artery and a location 4 cm downstream from the bifurcation. The electrical signals in both graphs were recorded using respective pairs of electrodes disposed around the circumference of the loop of a LASSO 1525 Variable Circular Mapping Catheter, manufactured by Biosense Webster. The signal shown in FIG. 15A was recorded using a pair of electrodes having a spacing of 8 mm from one another, and the signal shown in FIG. 15B was recorded using a pair of electrodes having a spacing of 26 mm from one another. It may be observed that the signal to noise ratio of the graph shown in FIG. 15B is greater than that of the graph shown in FIG. 15A. The data in the graphs indicate that, in order to facilitate the detection of a subject's ECG and/or blood pressure using electrical signal measured at the aorta, as described hereinabove, electrodes should be placed in contact with aorta having a spacing from one another around the circumference of the aorta of more than 10 mm, e.g., more than 15 mm, and the electrical signal of the aorta should be detected via the electrodes. Thus, for some applications of the present invention, electrodes are placed in contact with aorta, the electrodes having a spacing from one another around the circumference of the aorta of more than 10 mm, e.g., more than 15 mm, and the electrical signal of the aorta is detected via the electrodes. The subject's ECG signal, and/or blood pressure is derived from the detected signal.

For some applications, the techniques described herein are practiced in combination with techniques described in PCT Publication WO 07/013065 to Gross, which is incorporated herein by reference. For some applications, the techniques described herein are practiced in combination with the techniques described in PCT application WO 09/095918, entitled "Peristaltic pump for treatment of erectile dysfunction," to Gross, which claims priority from US Patent Application 2009/0198097 to Gross, the PCT application and the US application being incorporated herein by reference. For some applications, the techniques described herein are practiced in combination with the techniques described in U.S. Patent Application 2009/0198097 to Gross, which is incorporated herein by reference. For some applications, the techniques described herein are practiced in combination with the techniques described in U.S. 2011/0137370 to Gross, and/or in U.S. 2010/0305392 to Gross, both of which applications, are incorporated herein by reference.

For some applications, the methods described herein are performed in combination with the techniques described in PCT Application WO 09/095920 to Gross, which is incorporated herein by reference.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method, comprising:
    identifying a subject as suffering from a condition selected from the group consisting of congestive heart failure, diastolic heart failure, acute myocardial infarction, and hypertension; and
    in response to the identifying:
        placing an electrode on an aorta of the subject at an aortic site that is downstream of a bifurcation of the aorta with a left subclavian artery, between the bifurcation of the aorta with the left subclavian artery of the subject and a bifurcation of the aorta with a fifth intercostal artery of the subject; and
        treating the subject by electrically stimulating the aortic site by driving a current into the aortic site, via the electrode.

2. The method according to claim 1, wherein treating the subject comprises reducing ventricular pressure of the subject.

3. The method according to claim 1, wherein treating the subject comprises reducing aortic pressure of the subject.

4. The method according to claim 1, wherein treating the subject comprises reducing sympathetic tone of the subject.

5. The method according to claim 1, wherein treating the subject comprises increasing parasympathetic tone of the subject.

6. The method according to claim 1, wherein placing the electrode at the aortic site comprises implanting the electrode at the aortic site.

7. The method according to claim 1, wherein identifying the subject as suffering from the condition comprises identifying the subject as suffering from a condition selected from the group consisting of congestive heart failure, diastolic heart failure, and hypertension, and wherein placing the electrode at the aortic site comprises placing the electrode at the aortic site that is between the first and fifth intercostal arteries.

8. The method according to claim 1, wherein placing the electrode at the aortic site comprises placing the electrode at an aortic site that is between the bifurcation of the aorta with the left subclavian artery and a bifurcation of the aorta with a fourth intercostal artery of the subject.

9. The method according to claim 8, wherein placing the electrode at the aortic site comprises placing the electrode at an aortic site that is between the bifurcation of the aorta with the left subclavian artery and a bifurcation of the aorta with a first intercostal artery of the subject.

10. The method according to claim 1, further comprising detecting an electrical signal at the aortic site, and deriving from the electrical signal a physiological parameter of the subject selected from the group consisting of: blood pressure of the subject and an ECG signal of the subject.

11. The method according to claim 10, wherein detecting the electrical signal at the aortic site comprises detecting the electrical signal using at least two electrodes that are disposed around a circumference of the aorta at the aortic site at a distance of more than 10 mm from one another.

12. The method according to claim 10, wherein driving the current into the aortic site comprises driving the current into the aortic site responsively to the detected electrical signal.

13. The method according to claim 12, wherein deriving the physiological parameter comprises deriving the subject's ECG signal, and wherein driving the current into the aortic site comprises driving the current into the aortic site in coordination with a QRS complex of the subject's ECG signal.

14. The method according to claim 1, wherein placing the electrode at the aortic site comprises placing the electrode in contact with the aortic site of the subject's aorta by percutaneously inserting the electrode into the subject's body via a catheter, the method further comprising, subsequent to termination of the electrical stimulation, removing the electrode and the catheter from the subject's body.

15. The method according to claim 14, wherein identifying the subject as suffering from the condition comprises identifying the subject as suffering from acute myocardial infarction.

16. The method according to claim 15, further comprising, in response to identifying the subject, performing a percutaneous coronary intervention, wherein electrically stimulating the aortic site comprises driving the current into the aortic site, at least periodically, during the percutaneous coronary intervention, and for a period of time following the percutaneous coronary intervention.

17. The method according to claim 15, wherein driving the current into the aortic site comprises reducing afterload of the subject by driving the current into the aortic site via the electrode.

18. The method according to claim 15, wherein driving the current into the aortic site comprises reducing ventricular pressure of the subject by driving the current into the aortic site via the electrode.

19. The method according to claim 15, wherein driving the current into the aortic site comprises reducing aortic pressure of the subject by driving the current into the aortic site via the electrode.

20. The method according to claim 15, wherein driving the current into the aortic site comprises reducing sympathetic tone of the subject by driving the current into the aortic site via the electrode.

21. The method according to claim 15, wherein driving the current into the aortic site comprises increasing parasympathetic tone of the subject by driving the current into the aortic site via the electrode.

22. The method according to claim 15, wherein placing the electrode in contact with the aortic site comprises assessing a response of the subject to placement of the electrode at a plurality of sites, and selecting one of the plurality of sites as the aortic site in response to the assessing.

23. The method according to claim 15, wherein driving the current into the aortic site comprises reducing ventricular work and oxygen consumption of the subject by driving the current into the aortic site via the electrode.

24. The method according to claim 15, wherein driving the current into the aortic site comprises increasing myocardial perfusion of the subject by driving the current into the aortic site via the electrode.

25. The method according to claim 15, wherein driving the current into the aortic site comprises reducing a likelihood of the myocardium being damaged due to ischemia by driving the current into the aortic site via the electrode.

26. The method according to claim 15, wherein driving the current into the aortic site comprises reducing a likelihood of the myocardium being damaged due to reperfusion injury by driving the current into the aortic site via the electrode.

27. The method according to claim 1, wherein placing the electrode on the subject's aorta at the aortic site comprises placing the electrode inside the aorta at the aortic site.

28. The method according to claim 1, wherein placing the electrode on the subject's aorta at the aortic site comprises placing the electrode outside the aorta at the aortic site.

* * * * *